US012593012B2

(12) United States Patent
    Oosake

(10) Patent No.: US 12,593,012 B2
(45) Date of Patent: Mar. 31, 2026

(54) MEDICAL IMAGE PROCESSING DEVICE, MEDICAL IMAGE PROCESSING METHOD, AND ENDOSCOPE SYSTEM

(71) Applicant: FUJIFILM Corporation, Tokyo (JP)

(72) Inventor: Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/629,965

(22) Filed: Apr. 9, 2024

(65) Prior Publication Data

US 2024/0259534 A1     Aug. 1, 2024

Related U.S. Application Data

(63) Continuation of application No. 18/169,150, filed on Feb. 14, 2023, now Pat. No. 11,985,449, which is a
(Continued)

(30) Foreign Application Priority Data

May 14, 2018     (JP) ................................. 2018-093213

(51) Int. Cl.
    *G06T 7/60*          (2017.01)
    *A61B 1/00*          (2006.01)
    (Continued)

(52) U.S. Cl.
    CPC ......... *H04N 7/183* (2013.01); *A61B 1/00006* (2013.01); *A61B 1/000094* (2022.02);
    (Continued)

(58) Field of Classification Search
    CPC ...... H04N 7/183; H04N 23/50; H04N 23/555;
    A61B 1/00006; A61B 1/000094; A61B 1/0005; A61B 2090/364; G06T 7/0012; G06T 7/60; G06T 7/70; G06T 11/001; G06T 2207/10068; G06T 2207/30004; G06T 2207/10016; G06T 2207/20084; G06T 2207/30096; G06V 10/25; G06V 10/764; G06V 10/82; G06V 2201/03
    See application file for complete search history.

(56) References Cited

U.S. PATENT DOCUMENTS

| | | | |
|---|---|---|---|
| 2012/0220840 A1* | 8/2012 | Morita ................. | A61B 1/0638 |
| | | | 600/109 |
| 2014/0046131 A1* | 2/2014 | Morita ............... | A61B 1/00177 |
| | | | 600/109 |

* cited by examiner

*Primary Examiner* — Siamak Harandi
(74) *Attorney, Agent, or Firm* — JCIPRNET

(57) ABSTRACT

Provided are a medical image processing device, a medical image processing method, and an endoscope system that make it easy to compare a region of interest and its peripheral region with each other and make it unlikely to miss the region of interest if the region of interest in a time-series image is reported by using figures. A coordinates calculating unit (43) that calculates, on the basis of region-of-interest information indicating a region of interest in a time-series image, a plurality of sets of coordinates of interest on an outline of a polygon or circle having a symmetric shape that surrounds the region of interest. A reporting information display control unit (45B) that superposes figures on the basis of the calculated plurality of sets of coordinates of interest when superposing the figures for reporting the region of interest on the time-series image. Herein, the figures have a size that does not change with respect to a size of the region of interest.

20 Claims, 15 Drawing Sheets

Related U.S. Application Data continuation of application No. 17/081,993, filed on Oct. 27, 2020, now Pat. No. 11,616,931, which is a continuation of application No. PCT/JP2019/017650, filed on Apr. 25, 2019.

(51) Int. Cl.

| | |
|---|---|
| *G06T 7/00* | (2017.01) |
| *G06T 7/70* | (2017.01) |
| *G06T 11/00* | (2006.01) |
| *G06V 10/25* | (2022.01) |
| *G06V 10/764* | (2022.01) |
| *G06V 10/82* | (2022.01) |
| *H04N 7/18* | (2006.01) |
| *H04N 23/50* | (2023.01) |

(52) U.S. Cl.

CPC .......... *A61B 1/0005* (2013.01); *G06T 7/0012* (2013.01); *G06T 7/60* (2013.01); *G06T 7/70* (2017.01); *G06T 11/001* (2013.01); *G06V 10/25* (2022.01); *G06V 10/764* (2022.01); *G06V 10/82* (2022.01); *H04N 23/50* (2023.01); *G06T 2207/10068* (2013.01); *G06T 2207/30004* (2013.01); *G06V 2201/03* (2022.01); *H04N 23/555* (2023.01)

MEDICAL IMAGE PROCESSING DEVICE, MEDICAL IMAGE PROCESSING METHOD, AND ENDOSCOPE SYSTEM

CROSS-REFERENCE TO RELATED APPLICATIONS

This application is a continuation application of and claims the priority benefit of a prior application Ser. No. 18/169,150, filed on Feb. 14, 2023, now allowed. The prior application Ser. No. 18/169,150 is a continuation application of and claims the priority benefit of a prior application Ser. No. 17/081,993, filed on Oct. 27, 2020, which is a Continuation of PCT International Application No. PCT/JP2019/017650 filed on Apr. 25, 2019 claiming priority under 35 U.S.C § 119(a) to Japanese Patent Application No. 2018-093213 filed on May 14, 2018. Each of the above applications is hereby expressly incorporated by reference, in its entirety, into the present application.

BACKGROUND OF THE INVENTION

1. Field of the Invention

The present invention relates to a medical image processing device, a medical image processing method, and an endoscope system, and particularly to a technique for reporting a region of interest in a time-series image.

2. Description of the Related Art

In the medical field, inspections are performed by using an endoscope system. In recent years, it has been known that a time-series image (moving image) picked up by an endoscope-scope is displayed on a monitor while a region of interest such as a lesion region included in the time-series image is recognized through image analysis of the time-series image and is reported to support inspections.

If a lesion is detected in the image (time-series image) by a recognizer during an inspection using an endoscope, by surrounding the lesion region in the image displayed on the monitor by a frame, the lesion can be reported.

An endoscope image processing device described in WO2017/073338A includes a reporting unit and an enhancement processing unit. If a feature region such as a lesion part is detected by a detection unit, the reporting unit generates a first display image for reporting that a feature region is detected. The enhancement processing unit generates a second display image obtained by performing enhancement processing on the feature region.

The first display image generated by the reporting unit is formed of an observation image and a reporting image (e.g., a flag) to be displayed in a display region different from the display region of the observation image. When a flag is set (reporting image is displayed) on the first display image, a surgeon can observe the observation image more carefully and can visually find a lesion part by themselves.

The second display image generated by the enhancement processing unit is an observation image or a still image obtained by performing enhancement processing on the feature region within the observation image or the still image. The enhancement processing herein is processing for displaying the position of the feature region within the image, and is, for example, processing for displaying a marker image (square frame) surrounding a candidate lesion region.

WO2017/073338A further describes that the marker image is not limited to a square frame image and may be, for example, any frame image, such as a triangle, a circle, or a star. Furthermore, WO2017/073338A also describes that the marker image is not limited to a frame image surrounding the candidate lesion region and may be an image not surrounding the candidate lesion region as long as the position of the candidate lesion region can be indicated (paragraph [0031] in WO2017/073338A).

In addition, an image processing device described in JP2016-158681A acquires image data obtained by picking up an image of a tissue, and on the basis of the acquired image data, calculates, for each pixel, a score indicating the degree of seriousness of the lesion in the tissue displayed in the image represented by the image data, and marks a high-score region by adding a mark surrounding the region. FIG. 14 (c-1) in JP2016-158681A illustrates an example of adding marks formed of a plurality of reference numerals or figures (e.g., stars) arranged to surround a high-score region, and FIG. 14 (c-2) illustrates an example of adding a ring-shaped mark surrounding a high-score region.

Although WO2017/073338A describes that the marker image is not limited to a frame image surrounding the candidate lesion region and may be an image not surrounding the candidate lesion region, the image not surrounding the candidate lesion region indicates, for example, the position of the candidate lesion region by differing the brightness or color tone of the candidate lesion region from that of a peripheral region. Also in this case, since the brightness or color tone of the candidate lesion region differs, it is difficult to compare the lesion region and the periphery with each other.

In addition, according to the invention described in WO2017/073338A, since the first display image formed of an observation image and a reporting image to be displayed in a display region different from the display region of the observation image, although observation of the observation image is not interrupted by the reporting image, it is not possible to immediately check the region where the lesion region is present in the observation image by using only the reporting image. On the other hand, if the first display image is switched to the second display image, the switching operation is complicated, and if the first display image and the second display image are to be displayed concurrently, the display regions of the first display image and the second display image are reduced.

JP2016-158681A displays a marking image formed by arranging a plurality of arrows so as to overlay the marking image and surround a region where the score indicating the degree of seriousness of a lesion in a tissue is high. However, the score is calculated for each pixel, and on the basis of the calculation results, the plurality of arrows are arranged on a boundary of the high-score region. This increases the number of arrows, and it may be difficult in some cases to compare the region with a high degree of seriousness and its periphery with each other.

SUMMARY OF THE INVENTION

If a lesion region in an observation image is surrounded by a frame image by using, for example, a square frame image as a marker image, as in the second display image described in WO2017/073338A, it may be difficult to be compared with its periphery.

The present invention has been made in view of such circumstances, and an object is to provide a medical image processing device, a medical image processing method, and an endoscope system that make it easy to compare a region of interest and its peripheral region with each other and make it unlikely to miss the region of interest if the region of interest in a time-series image is reported by using figures.

In order to achieve the above object, a medical image processing device according to an aspect of the present invention includes: a coordinates calculating unit that calculates, on the basis of region-of-interest information indicating a region of interest in a time-series image, a plurality of sets of coordinates of interest on an outline of a polygon or circle having a symmetric shape that surrounds the region of interest; and a reporting information display control unit that superposes figures on the time-series image on the basis of the plurality of sets of coordinates of interest, in which the figures have a size that does not change with respect to a size of the region of interest.

According to the aspect of the present invention, on the basis of the region-of-interest information indicating the region of interest in the time-series image, the plurality of sets of coordinates of interest on the outline of the polygon or circle having the symmetric shape that surrounds the region of interest are calculated. When the figures are superposed on the time-series image, each of the figures is superposed on the time-series image on the basis of the calculated plurality of sets of coordinates of interest. The figures have a size that does not change with respect to a size of the region of interest. The size of the figures does not change even if the positions for superposition change in accordance with the size of the region of interest (interval between the sets of coordinates of interest).

Thus, the interval between the figures superposed on the time-series image on the basis of the plurality of sets of coordinates of interest are separated away in accordance with the size of the region of interest. If the region of interest becomes larger, the plurality of figures become more away from one another and less noticeable, and comparison between the large region of interest with its peripheral region is not interrupted. On the other hand, if the region of interest becomes smaller, the plurality of figures become closer to one another and more noticeable, and the small region of interest is unlikely to be missed.

The medical image processing device according to the aspect of the present invention preferably further includes a time-series image acquiring unit that acquires the time-series image including a photographic subject image; a region-of-interest detecting unit that detects the region of interest from the time-series image acquired by the time-series image acquiring unit; and a region-of-interest information acquiring unit that acquires the region-of-interest information indicating the region of interest from the region-of-interest detecting unit. For example, the region-of-interest detecting unit may calculate, through learning, a feature amount from the image and may apply a convolutional neural network (CNN) that performs recognition processing of the region of interest.

In a medical image processing device according to still another aspect of the present invention, the coordinates calculating unit preferably calculates, as the plurality of sets of coordinates of interest, sets of coordinates of vertexes of the polygon.

In a medical image processing device according to still another aspect of the present invention, the coordinates calculating unit preferably calculates, as the plurality of sets of coordinates of interest, sets of coordinates of midpoints of sides of the polygon.

In a medical image processing device according to still another aspect of the present invention, the polygon is preferably a polygon in which the region of interest is inscribed. Thus, the plurality of figures can be arranged so as to surround the region of interest.

In a medical image processing device according to still another aspect of the present invention, the polygon is preferably a square.

In a medical image processing device according to still another aspect of the present invention, the coordinates calculating unit preferably calculates, as the plurality of sets of coordinates of interest, sets of coordinates of points at which a circumference of the circle is equally divided into a plurality of parts. In this case, the number of the sets of coordinates of interest corresponds to the number of the points at which the circumference is equally divided.

In a medical image processing device according to still another aspect of the present invention, the circle is preferably a circle in which the region of interest is inscribed. Thus, the plurality of figures can be arranged so as to surround the region of interest.

A medical image processing device according to still another aspect of the present invention preferably includes: a coordinates storage unit that stores the sets of coordinates of interest calculated by the coordinates calculating unit as sets of reference coordinates; and a determination unit that compares the sets of reference coordinates stored in the coordinates storage unit and the sets of coordinates of interest calculated by the coordinates calculating unit with each other and determines whether a change amount between the sets of reference coordinates and the sets of coordinates of interest exceeds a threshold. If the determination unit determines that the change amount is less than or equal to the threshold, the reporting information display control unit preferably superposes the figures on the basis of the sets of reference coordinates stored in the coordinates storage unit, and, if the determination unit determines that the change amount exceeds the threshold, the reporting information display control unit preferably superposes the figures on the basis of the sets of coordinates of interest calculated by the coordinates calculating unit and updates the sets of reference coordinates stored in the coordinates storage unit to the sets of coordinates of interest calculated by the coordinates calculating unit.

Although the size or position of the region of interest in the time-series image may vary over time, if the figures are made to follow in accordance with slight variations of the region of interest, the figures move frequently and are difficult to move. Accordingly, if the change amount between the newly calculated sets of coordinates of interest and the temporarily stored sets of reference coordinates is less than or equal to the threshold, the figures are superposed on the basis of the sets of reference coordinates so as to suppress movement of the figures. If the change amount exceeds the threshold, the figures are superposed on the basis of the calculated sets of coordinates of interest, and the sets of reference coordinates are updated to the calculated sets of coordinates of interest.

A medical image processing device according to still another aspect of the present invention preferably includes: a coordinates storage unit that stores the sets of coordinates of interest calculated by the coordinates calculating unit as sets of reference coordinates and stores coordinates located at a center of the sets of reference coordinates as first center coordinates; and a determination unit that compares the first center coordinates stored in the coordinates storage unit and second center coordinates located at a center of the sets of coordinates of interest calculated by the coordinates calculating unit with each other and determines whether a change amount between the first center coordinates and the second center coordinates exceeds a threshold. If the determination unit determines that the change amount is less than or equal to the threshold, the reporting information display control unit preferably superposes the figures on the basis of the sets of reference coordinates stored in the coordinates storage unit, and, if the determination unit determines that the change amount exceeds the threshold, the reporting information display control unit preferably superposes the figures on the basis of the sets of coordinates of interest calculated by the coordinates calculating unit and updates the sets of reference coordinates and the first center coordinates stored in the coordinates storage unit to the sets of coordinates of interest calculated by the coordinates calculating unit and the second center coordinates.

A medical image processing device according to still another aspect of the present invention preferably includes: a coordinates storage unit that stores the sets of coordinates of interest calculated by the coordinates calculating unit as sets of reference coordinates; and a determination unit that compares the sets of reference coordinates stored in the coordinates storage unit and the sets of coordinates of interest calculated by the coordinates calculating unit with each other and determines whether the sets of coordinates of interest are inside the sets of reference coordinates. If the determination unit determines that the sets of coordinates of interest are inside the sets of reference coordinates, the reporting information display control unit preferably superposes the figures on the basis of the sets of reference coordinates stored in the coordinates storage unit, and, if the determination unit determines that the sets of coordinates of interest are outside the sets of reference coordinates, the reporting information display control unit preferably superposes the figures on the basis of the sets of coordinates of interest calculated by the coordinates calculating unit and updates the sets of reference coordinates stored in the coordinates storage unit to the sets of coordinates of interest calculated by the coordinates calculating unit.

In a medical image processing device according to still another aspect of the present invention, the figures are preferably a plurality of figures corresponding to the plurality of sets of coordinates of interest obtained by rotating a single figure or reversing a single figure. Thus, the plurality of figures can be generated from a single figure without individually preparing the plurality of figures.

In a medical image processing device according to still another aspect of the present invention, if the region of interest includes a plurality of regions of interest, the reporting information display control unit preferably assigns figures having different shapes to the plurality of regions of interest as the figures to be added to the time-series image. Thus, it becomes easy to distinguish the plurality of regions of interest by the figures having different shapes, and it becomes easy to visually follow the plurality of regions of interest when the plurality of regions of interest move.

In a medical image processing device according to still another aspect of the present invention, if the region of interest includes a plurality of regions of interest, it is preferable to assign figures having different colors to the plurality of regions of interest as the figures to be added to the time-series image. Thus, it becomes easy to distinguish the plurality of regions of interest by the figures having different colors, and it becomes easy to visually follow the plurality of regions of interest when the plurality of regions of interest move.

In a medical image processing device according to still another aspect of the present invention, the figures are preferably joined to one another if an interval between the plurality of sets of coordinates of interest is a predetermined interval corresponding to a size of the figures and are preferably separated away from one another in accordance with the interval between the plurality of sets of coordinates of interest if the interval exceeds the predetermined interval. In a case where each figure has a shape along the outline of the polygon or circle that surrounds the region of interest, if the interval between the plurality of sets of coordinates of interest is the predetermined interval corresponding to the size of the figures, the figures are joined to one another to become a polygon or circle that surrounds the region of interest.

An endoscope system according to still another aspect of the present invention includes: the above medical image processing device; an endoscope that picks up the time-series image; and a display control unit that displays the time-series image picked up by the endoscope on a display, in which the reporting information display control unit superposes and displays the figures for reporting the region of interest on the time-series image displayed on the display.

A medical image processing method according to still another aspect of the present invention includes: a step of calculating, on the basis of region-of-interest information indicating a region of interest in a time-series image, a plurality of sets of coordinates of interest on an outline of a polygon or circle having a symmetric shape that surrounds the region of interest; and a step of superposing figures on the time-series image on the basis of the plurality of sets of coordinates of interest, in which the figures have a size that does not change with respect to a size of the region of interest.

According to the present invention, in a case where a region of interest in a time-series image is reported by using figures, the figures are made less noticeable to report a large region of interest to make it easy to compare the large region of interest with its peripheral region and are made more noticeable to report a small region of interest to make it unlikely to miss the small region of interest.

BRIEF DESCRIPTION OF THE DRAWINGS

FIGS. 8A to 8E illustrate five types of reporting information applied if a polygon having a symmetric shape that surrounds a region of interest is a square;

DESCRIPTION OF THE PREFERRED EMBODIMENTS

Hereinafter, preferred embodiments of a medical image processing device, a medical image processing method, and an endoscope system according to the present invention will be described with reference to the accompanying drawings.
Overall Configuration of Endoscope System FIG. 1 illustrates an overview of an overall configuration of an endoscope system 9 including a medical image processing device according to the present invention.

Figure 1:
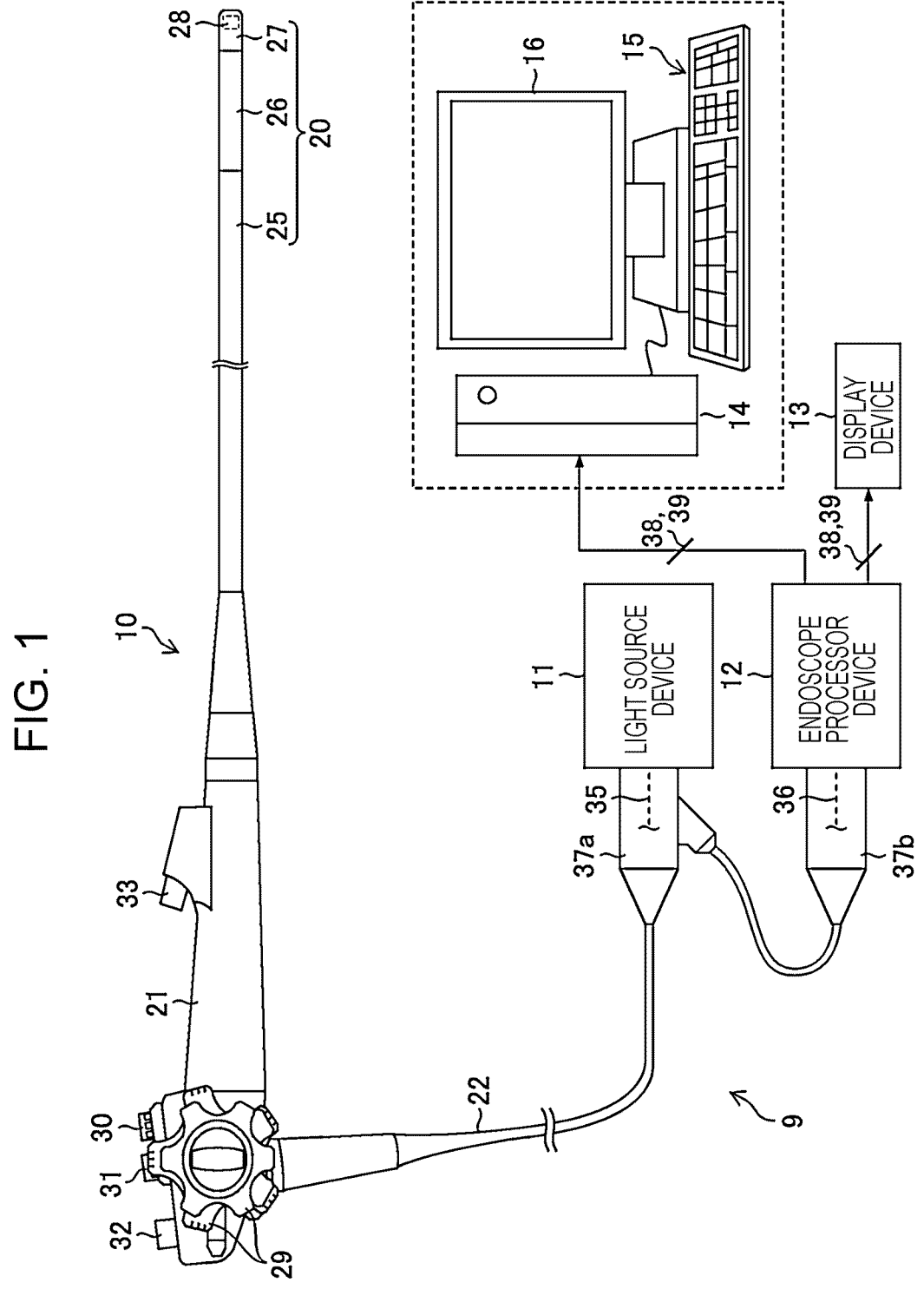
FIG. 1 illustrates an overview of an overall configuration of an endoscope system 9 including a medical image processing device according to the present invention.

As illustrated in FIG. 1, the endoscope system 9 includes an endoscope 10, which is an electronic endoscope, a light source device 11, an endoscope processor device 12, a display device 13, a medical image processing device 14, an operating unit 15, and a display 16.

The endoscope 10 corresponds to a time-series image acquiring unit that acquires a time-series image including a photographic subject image and is a flexible endoscope, for example. The endoscope 10 has an insertion part 20, a handheld operating unit 21, and a universal cord 22. The insertion part 20 is inserted into a subject and has a distal end and a base end. The handheld operating unit 21 is disposed continuously with the base end side of the insertion part 20 and held by a surgeon to perform various operations. The universal cord 22 is disposed continuously with the handheld operating unit 21.

The entire insertion part 20 is formed to have a small diameter and an elongated shape. The insertion part 20 is constituted by a soft part 25, a bending part 26, and a distal end part 27, which are disposed continuously with each other in this order from the base end side to the distal end side. The soft part 25 has flexibility. The bending part 26 is bendable by an operation of the handheld operating unit 21. An imaging optical system (objective lens), an imaging element 28, and the like, which are not illustrated, are incorporated in the distal end part 27.

The imaging element 28 is an imaging element of a complementary metal oxide semiconductor (CMOS) type or a charge coupled device (CCD) type. Image light of a part to be observed is incident on an imaging surface of the imaging element 28 through an observation window and the objective lens. The observation window, which is not illustrated, is open on a distal end surface of the distal end part 27, and the objective lens, which is not illustrated, is disposed behind the observation window. The imaging element 28 picks up the image light of the part to be observed, which is incident on the imaging surface (converts the image light into an electric signal) and outputs an image signal.

The handheld operating unit 21 is provided with various operating members to be operated by a surgeon. Specifically, the handheld operating unit 21 is provided with two types of bending operation knobs 29 to be used for a bending operation of the bending part 26, an air/water supply button 30 for air supply/water supply operations, and a suction button 31 for a suction operation. The handheld operating unit 21 is further provided with a still image pick-up command unit 32 for issuing a command for picking up a still image 39 of the part to be observed and a treatment tool introduction port 33 for inserting a treatment tool (not illustrated) into a treatment tool insertion path (not illustrated) that penetrates through the insertion part 20.

The universal cord 22 is a connection cord for connecting the endoscope 10 to the light source device 11. The universal cord 22 contains a light guide 35 that penetrates through the insertion part 20, a signal cable 36, and a fluid tube (not illustrated). In addition, an end portion of the universal cord 22 is provided with a connector 37a that is connected to the light source device 11 and a connector 37b that branches off from the connector 37a and is connected to the endoscope processor device 12.

Since the connector 37a is connected to the light source device 11, the light guide 35 and the fluid tube (not illustrated) are inserted into the light source device 11. Thus, through the light guide 35 and the fluid tube (not illustrated), necessary illumination light, water, and gas are supplied from the light source device 11 to the endoscope 10. As a result, the part to be observed is irradiated with the illumination light from an illumination window (not illustrated) on the distal end surface of the distal end part 27. In accordance with a pressing operation on the above-described air/water supply button 30, the gas or water is injected from an air/water supply nozzle (not illustrated) on the distal end surface of the distal end part 27 to the observation window (not illustrated) on the distal end surface.

Since the connector 37b is connected to the endoscope processor device 12, the signal cable 36 is electrically connected to the endoscope processor device 12. Thus, through the signal cable 36, an image signal of the part to be observed is output from the imaging element 28 of the endoscope 10 to the endoscope processor device 12, and also, a control signal is output from the endoscope processor device 12 to the endoscope 10.

The light source device 11 supplies the illumination light through the connector 37a to the light guide 35 of the endoscope 10. As the illumination light, light in various wavelength ranges in accordance with an observation purpose, such as white light (light in a white wavelength range or light in a plurality of wavelength ranges), light in one or more specific wavelength ranges, or a combination thereof is selected. Note that the specific wavelength range is narrower than the white wavelength range.

A first example of the specific wavelength range is, for example, a blue range or a green range in a visible range. The wavelength range of the first example includes a wavelength range of greater than or equal to 390 nm and less than or equal to 450 nm or greater than or equal to 530 nm and less than or equal to 550 nm, and light of the first example has a peak wavelength in the wavelength range of greater than or equal to 390 nm and less than or equal to 450 nm or greater than or equal to 530 nm and less than or equal to 550 nm.

A second example of the specific wavelength range is, for example, a red range in a visible range. The wavelength range of the second example includes a wavelength range of greater than or equal to 585 nm and less than or equal to 615 nm or greater than or equal to 610 nm and less than or equal to 730 nm, and light of the second example has a peak wavelength in the wavelength range of greater than or equal to 585 nm and less than or equal to 615 nm or greater than or equal to 610 nm and less than or equal to 730 nm.

A third example of the specific wavelength range includes a wavelength range in which oxidized hemoglobin and reduced hemoglobin have different absorption coefficients, and light of the third example has a peak wavelength in the wavelength range in which oxidized hemoglobin and reduced hemoglobin have different absorption coefficients. The wavelength range of the third example includes a wavelength range of 400±10 nm, 440±10 nm, 470±10 nm, or greater than or equal to 600 nm and less than or equal to 750 nm, and light of the third example has a peak wavelength in the wavelength range of 400±10 nm, 440±10 nm, 470±10 nm, or greater than or equal to 600 nm and less than or equal to 750 nm.

A fourth example of the specific wavelength range is the wavelength range (from 390 nm to 470 nm) of excitation light that is used for observing fluorescence (fluorescence observation) emitted by a fluorescent material in a living body and that excites the fluorescent material.

A fifth example of the specific wavelength range is the wavelength range of infrared light. The wavelength range of the fifth example includes a wavelength range of greater than or equal to 790 nm and less than or equal to 820 nm or greater than or equal to 905 nm and less than or equal to 970 nm, and light of the fifth example has a peak wavelength in the wavelength range of greater than or equal to 790 nm and less than or equal to 820 nm or greater than or equal to 905 nm and less than or equal to 970 nm.

The endoscope processor device 12 controls operations of the endoscope 10 through the connector 37b and the signal cable 36. In addition, on the basis of the image signal acquired from the imaging element 28 of the endoscope 10 through the connector 37b and the signal cable 36, the endoscope processor device 12 generates a time-series image (also referred to as "moving image 38") formed of time-series frame images 38a including the photographic subject image. Furthermore, if the still image pick-up command unit 32 is operated in the handheld operating unit 21 of the endoscope 10, concurrently with the generation of the moving image 38, one frame image in the moving image 38 is acquired as the still image 39 in accordance with the timing of an imaging command.

The moving image 38 and the still image 39 are medical images obtained by picking up images of the inside of the subject, that is, a living body. In addition, if the moving image 38 and the still image 39 are images obtained with the above-described light in the specific wavelength range (special light), both are special light images. In addition, the endoscope processor device 12 outputs the generated moving image 38 and the still image 39 to each of the display device 13 and the medical image processing device 14.

Note that the endoscope processor device 12 may generate (acquire) the special light image having information about the above-described specific wavelength range on the basis of a usual light image obtained with the above-described white light. In this case, the endoscope processor device 12 functions as a special light image acquiring unit. Then, the endoscope processor device 12 obtains a signal in the specific wavelength range by performing calculation based on color information of red, green, and blue [RGB (Red, Green, Blue)] or cyan, magenta, and yellow [CMY (Cyan, Magenta, Yellow)] included in the usual light image.

On the basis of, for example, at least one of the usual light image obtained with the above-described white light and the special light image obtained with the above-described light in the specific wavelength range (special light), the endoscope processor device 12 may generate a feature amount image such as a known oxygen saturation image. In this case, the endoscope processor device 12 functions as a feature amount image generating unit. Note that each of the moving image 38 and the still image 39 including the above-described in-living-body image, the usual light image, the special light image, and the feature amount image is a medical image obtained by converting results of imaging or measuring of a human body into an image for the purpose of image diagnosis or inspection.

The display device 13 is connected to the endoscope processor device 12 and displays the moving image 38 and the still image 39 input from the endoscope processor device 12. A surgeon (physician) operates the insertion part 20 back and forth, for example, while viewing the moving image 38 displayed on the display device 13, and, if a lesion or the like is found at the part to be observed, the surgeon (physician) operates the still image pick-up command unit 32 to pick up a still image of the part to be observed for diagnosis, biopsy, or the like.

Medical Image Processing Device

The medical image processing device 14 mainly reports a region of interest included in a time-series image to a surgeon, and, for example, a personal computer is used as the medical image processing device 14 in this embodiment. In addition, a keyboard, a mouse, or the like connected to the personal computer via wired or wireless connection is used as the operating unit 15, and any monitor, such as a liquid crystal monitor that can be connected to the personal computer, is used as the display 16.

Functions of Medical Image Processing Device

First Embodiment of Medical Image Processing Device 14

Figure 2:
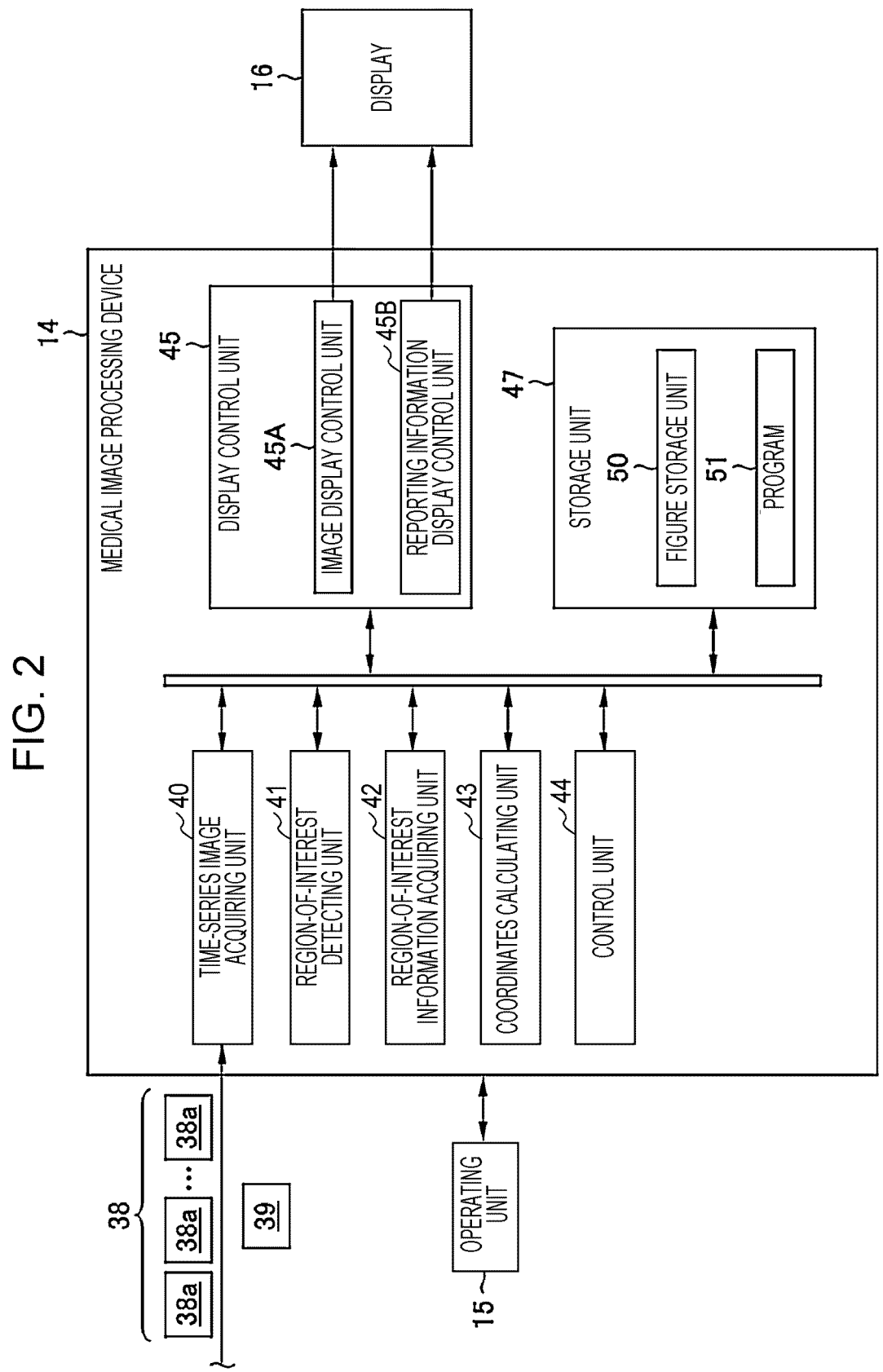
FIG. 2 is a block diagram illustrating a first embodiment of a medical image processing device 14.

FIG. 2 is a block diagram illustrating a first embodiment of the medical image processing device 14.

The medical image processing device 14 illustrated in FIG. 2 is mainly constituted by a time-series image acquiring unit 40, a region-of-interest detecting unit 41, a region-of-interest information acquiring unit 42, a coordinates calculating unit 43, a control unit 44, a display control unit 45, and a storage unit 47.

On the basis of a program (medical image processing program) 51 stored in the storage unit 47, the control unit 44 generally controls the time-series image acquiring unit 40, the region-of-interest detecting unit 41, the region-of-interest information acquiring unit 42, the coordinates calculating unit 43, and the display control unit 45 and functions as part of these units.

The storage unit 47 is a part that stores detection results obtained by the region-of-interest detecting unit 41 and stores a picked-up still image 39, and also stores information or the like related to various controls of a figure storage unit 50 that stores figures constituting the reporting information, the program 51, and the medical image processing device 14.

The time-series image acquiring unit 40 acquires, from the endoscope processor device 12, a time-series image (moving image 38 picked up by the endoscope 10 in this example), formed of time-series frame images 38a including a photographic subject image, by using an image input/output interface, which is not illustrated, connected to the endoscope processor device 12 (FIG. 1) via wired or wireless connection. In addition, if the above-described still image 39 is picked up while the moving image 38 is being picked up by the endoscope 10, the time-series image acquiring unit 40 acquires the moving image 38 and the still image 39 from the endoscope processor device 12.

Note that, instead of directly acquiring the moving image 38 from the endoscope processor device 12, the time-series image acquiring unit 40 may acquire the moving image 38 via any information storage medium, such as a memory card or a hard disk apparatus. In addition, the time-series image acquiring unit 40 may acquire, via the Internet, the moving image 38 uploaded on a server, database, or the like on the Internet.

The region-of-interest detecting unit 41 is a part that detects a region of interest from the moving image 38 picked up during observation of a body cavity. In this example, frame images (or thinned frame images at certain intervals) of the moving image 38 are sequentially input, and the region-of-interest detecting unit 41 calculates, through learning, a feature amount of the input images, includes a convolutional neural network (CNN) that performs recognition processing of the region of interest within an image, and calculates a feature amount from color information, a pixel value gradient, or the like within the image. By using the calculated feature amount, the region-of-interest detecting unit 41 detects the region of interest such as a lesion in the image, and can further acquire a recognition result of, for example, category classification as to whether the detected region of interest belongs to which of a plurality of categories about the lesion, such as "tumorous", "non-tumorous", and "others".

Note that the region-of-interest detecting unit 41 is not limited to the one that detects the region of interest by the CNN, but may detect the region of interest by analyzing a feature amount of the color, pixel value gradient, shape, size, or the like of the image through image processing. In addition, the region of interest may be, not only the lesion, but also a treatment scar, a treatment tool, or the like.

If the region-of-interest detecting unit 41 detects the region of interest, the region-of-interest information acquiring unit 42 acquires region-of-interest information indicating the region of interest from the region-of-interest detecting unit 41. The region-of-interest information can be, for example, information of coordinates of an outline of the region of interest in the image.

Figure 3:
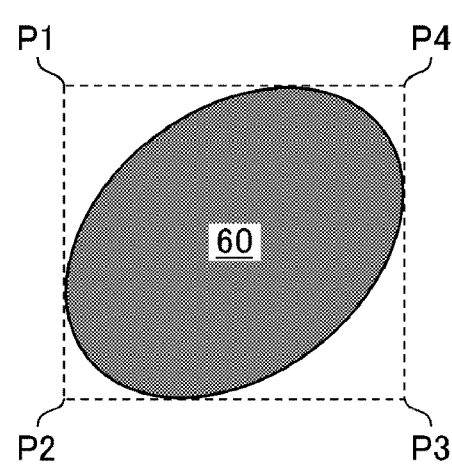
FIG. 3 is a diagram used for describing a coordinates calculating unit 43 and a reporting information display control unit 45B of the medical image processing device 14.
Figure 3:
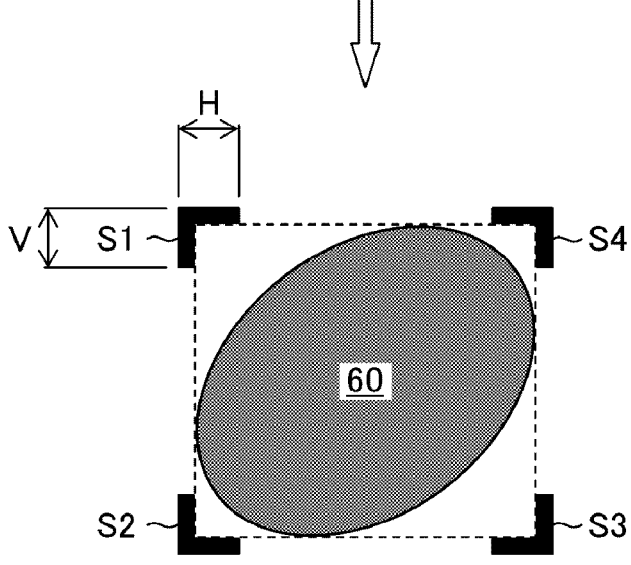

The coordinates calculating unit 43 acquires the region-of-interest information from the region-of-interest information acquiring unit 42 and, on the basis of the acquired region-of-interest information, calculates a plurality of sets of coordinates of interest on an outline of a polygon or circle having a symmetric shape that surrounds the region of interest. In this example, the coordinates calculating unit 43 calculates, as sets of coordinates of interest P1 to P4, coordinates of four vertexes of a square (rectangle indicated by the broken line) in which a region of interest 60 is inscribed as illustrated in FIG. 3.

The display control unit 45 displays the moving image 38 on the display 16 and also displays reporting information (figures) for reporting the region of interest included in the moving image 38 to a surgeon, and includes an image display control unit 45A and a reporting information display control unit 45B.

The image display control unit 45A receives the time-series image (moving image 38) acquired by the time-series image acquiring unit 40, and on the basis of the received moving image 38, generates image data for display and outputs it to the display 16. The display 16 displays an endoscope image (the usual light image or the special light image of the moving image) based on the image data for display received from the image display control unit 45A.

On the basis of the plurality of sets of coordinates of interest (the four sets of coordinates of interest P1 to P4 in this example) calculated by the coordinates calculating unit 43, the reporting information display control unit 45B superposes, on the endoscope image, reporting information constituted by a plurality of figures that each report the region of interest and have the same number as the number of the plurality of sets of coordinates of interest.

For example, in a case where the sets of coordinates of interest P1 to P4 indicating the vertexes of a rectangle that surrounds the region of interest 60 illustrated in FIG. 3 are input, the reporting information display control unit 45B superposes and displays the reporting information constituted by the following figures.

From the set of coordinates of interest P1, the reporting information display control unit 45B generates a fixed-length line segment H directed rightward in the horizontal direction and a fixed-length line segment V directed downward in the vertical direction in FIG. 3 and generates an L-shaped figure S1 formed of these line segments H and V. In the same manner, for the other sets of coordinates of interest P2, P3, and P4, the reporting information display control unit 45B generates figures S2, S3, and S4 corresponding to the sets of coordinates of interest P2, P3, and P4, respectively.

Each of these figures S1 to S4 is a figure fixed to a certain size. Note that the line segments H and V in the figure S1 in this example have an identical length and a fixed thickness. In addition, in a case where the image has a horizontal direction size of 1280 pixels and a vertical direction size of 1024 pixels for example, the length of the line segments H and V is preferably 24 pixels from the coordinates of interest P1.

The reporting information display control unit 45B outputs image data indicating the generated figures S1 to S4 to the display 16.

By receiving the image data indicating the figures S1 to S4, the display 16 can superpose and display, on the image, the reporting information constituted by the figures S1 to S4, which report the region of interest in the image being displayed.

FIGS. 4 to 7 each illustrate the image and the reporting information (figures) displayed on the display 16, and the images and the reporting information are in a state where time elapses from FIG. 4 to FIG. 7.

That is, the images illustrated in FIGS. 4 to 7 illustrate part of the time-series image in a time-series manner if the distal end of the endoscope 10 is made to gradually approach the region of interest. Images of regions of interest 61, 62, 63, and 64 are picked up to be gradually enlarged.

Figure 4:
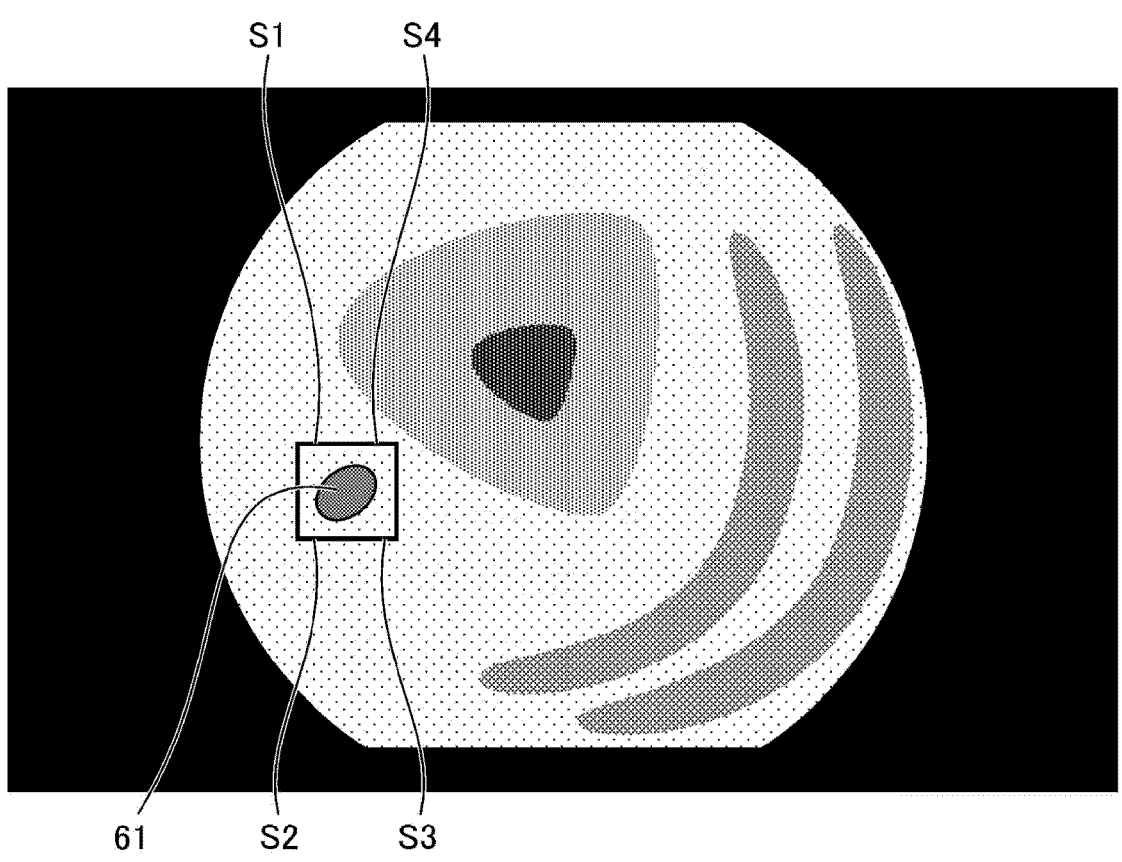
FIG. 4 illustrates an image and reporting information displayed on a display 16.

In the image illustrated in FIG. 4, since the region of interest 61 is away from the distal end of the endoscope 10, the picked-up image of the region of interest 61 is small.

Since the region of interest 61 is small and the interval between the sets of coordinates of interest is less than or equal to a predetermined interval (the length of 48 pixels in this example) corresponding to the size of the figures S1 to S4, the figures S1 to S4 illustrated in FIG. 4 are joined to one another to constitute a rectangular frame. Note that for the reporting information constituted by the figures S1 to S4, the length of each size is preferably limited so as not to be less than or equal to the predetermined interval (the length of 48 pixels in this example) corresponding to the size of the figures S1 to S4. Otherwise, the reporting information is not noticeable due to an extremely small size, and a small region of interest may be more likely to be missed.

Figure 5:
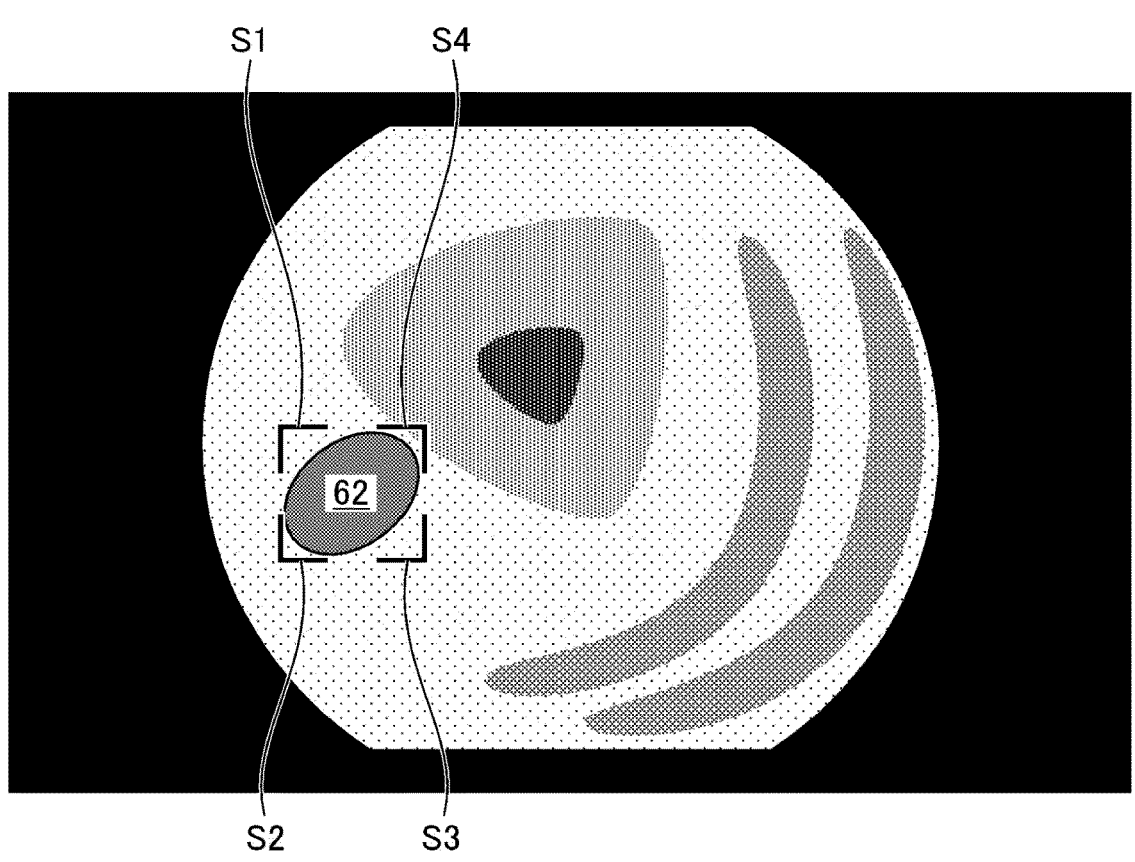
FIG. 5 illustrates an image and reporting information displayed on the display 16 after the time has passed from the state illustrated in FIG. 4.

Since the region of interest 62 is larger than the region of interest 61 and the interval between the sets of coordinates of interest is also increased, the four figures S1 to S4 illustrated in FIG. 5 are separated from one another in accordance with the size of the region of interest 62. Although the four figures S1 to S4 are separated from one another in FIG. 5, the region of interest 62 is comparatively small, and the figures S1 to S4 become closer to one another and more noticeable.

Figure 6:
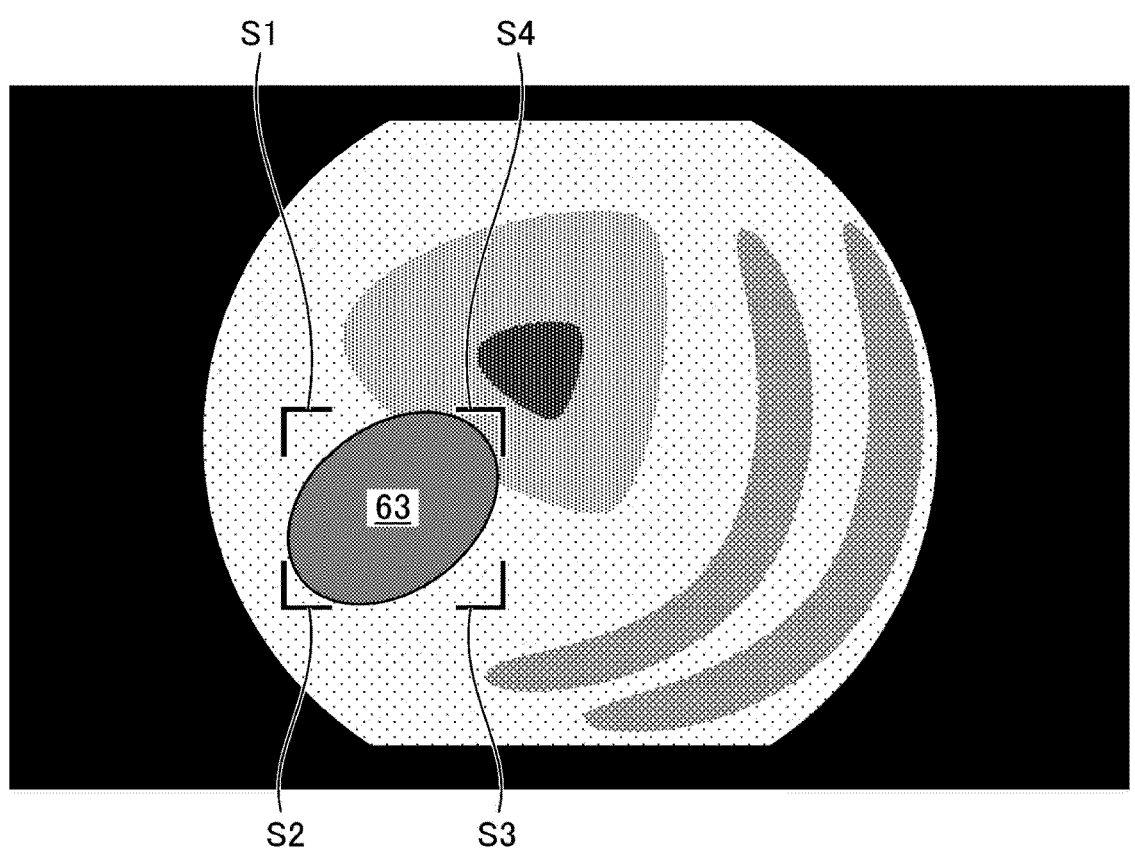
FIG. 6 illustrates an image and reporting information displayed on the display 16 after the time has passed from the state illustrated in FIG. 5.

On the other hand, since the region of interest 63 is larger than the region of interest 62 and the interval between the sets of coordinates of interest is further increased, the four figures S1 to S4 illustrated in FIG. 6 are separated from one another in accordance with the size of the region of interest 63. Since the region of interest 64 is larger than the region of interest 63, the four figures S1 to S4 illustrated in FIG. 7 are separated from one another in accordance with the size of the region of interest 63.

Figure 7:
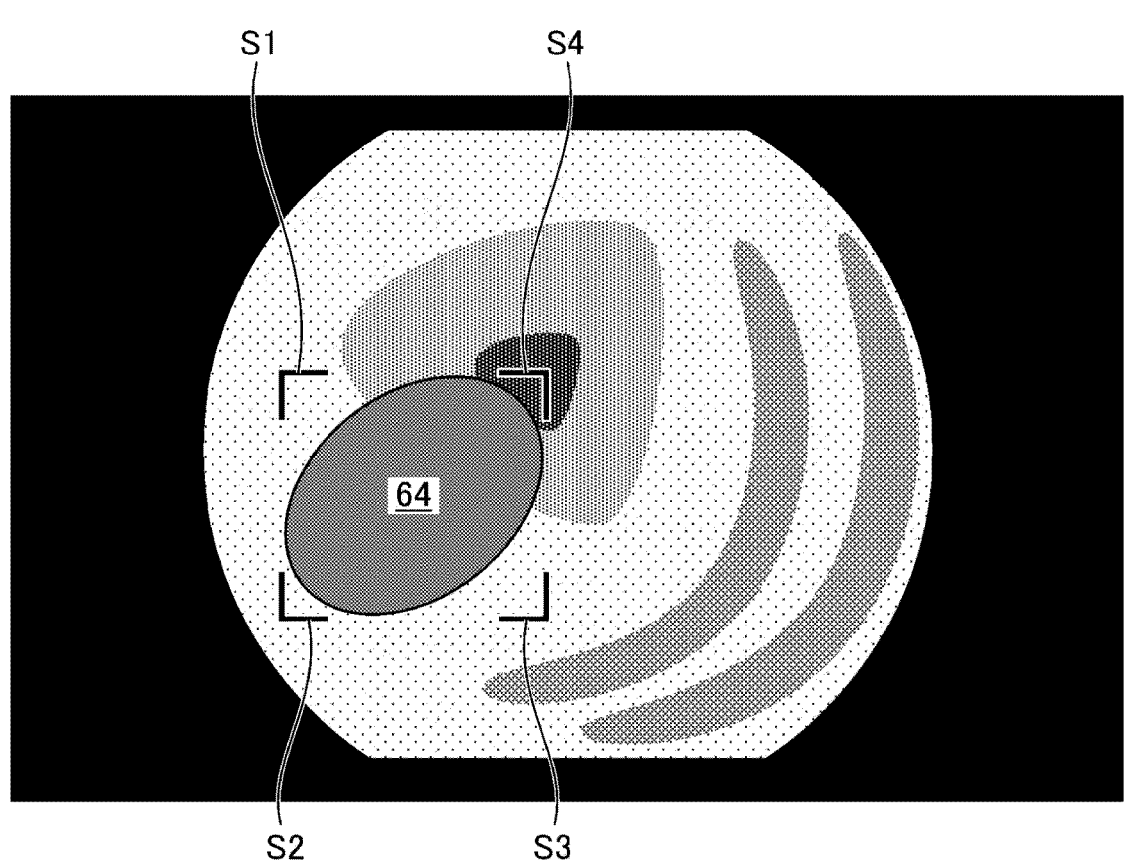
FIG. 7 illustrates an image and reporting information displayed on the display 16 after the time has passed from the state illustrated in FIG. 6.

The figures S1 to S4 illustrated in FIGS. 6 and 7 are separated away from one another in accordance with the size of the regions of interest 63 and 64, and the figures S1 to S4 become more away from one another and less noticeable, and comparison between the region of interest 63 with its peripheral region and between the region of interest 64 and its peripheral region is not interrupted.

Note that the coordinates calculating unit 43 illustrated in FIG. 2 calculates, as the sets of coordinates of interest P1 to P4, the sets of coordinates of the four vertexes of the rectangle in which the region of interest 60 is inscribed as illustrated in FIG. 3. Without limitation to this, the rectangle in which the region of interest 60 is inscribed may be enlarged at a certain magnification (e.g., 1.2 times), and the vertexes of the enlarged rectangle may be calculated as the sets of coordinates of interest, or the sets of coordinates of the four vertexes of the rectangle in which the region of interest 60 is inscribed may be moved by a certain amount in the direction to be separated away from one another, and the moved sets of coordinates may be calculated as the sets of coordinates of interest.

In addition, the reporting information display control unit 45B is not limited to the case of generating the figures S1 to S4 from the fixed-length line segments H and V. The figures S1 to S4 may be read out from the figure storage unit 50 that stores the figures S1 to S4 (icon images) constituting the reporting information, and on the basis of the sets of coordinates of interest P1 to P4, the figures S1 to S4 may be arranged at positions corresponding to the sets of coordinates of interest P1 to P4 so that the reporting information constituted by the figures S1 to S4 are superposed on an image.

Variations of Reporting Information (Figures)

FIGS. 8A to 8E illustrate five types of reporting information displayed along an outline of a square having a symmetric shape that surrounds the region of interest.

Figures 8A, 8B, 8C, 8D, 8E:
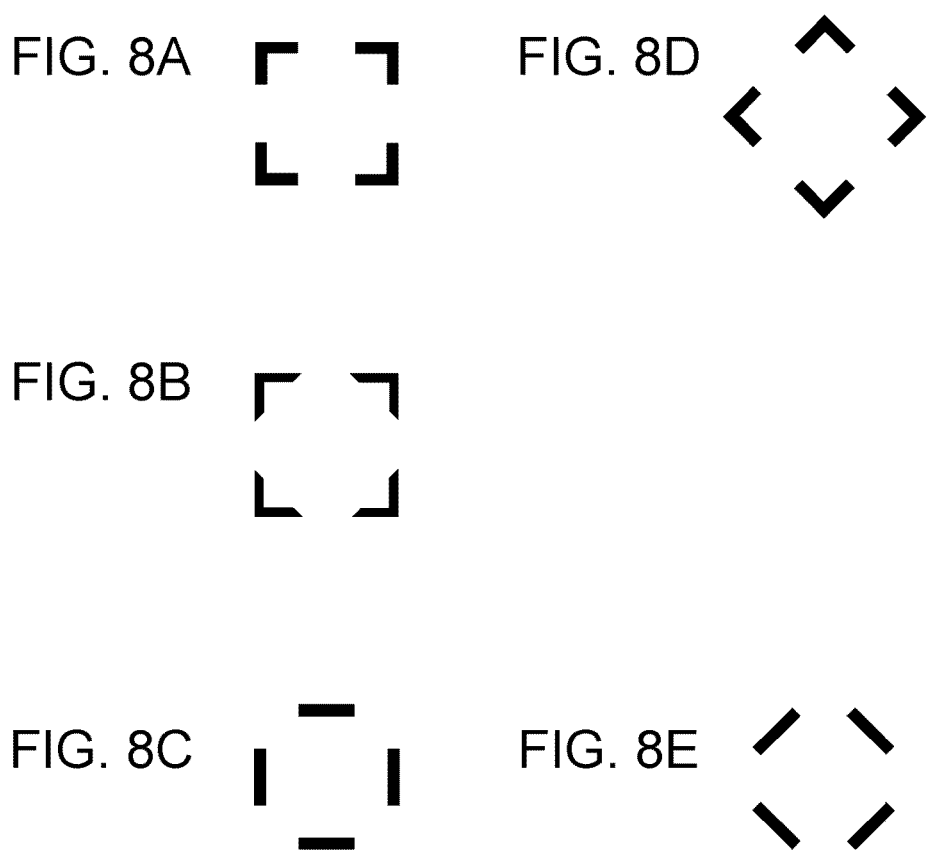

The reporting information illustrated in FIG. 8A is reporting information constituted by the figures S1 to S4 illustrated in FIG. 3 and the like, and the reporting information in FIG. 8B is a modification of the reporting information in FIG. 8A.

The reporting information in FIG. 8C is applied when sets of the coordinates of midpoints of the respective sides of the rectangle that surrounds the region of interest are set as the sets of coordinates of interest and is constituted by figures of line segments of a certain length.

Each of the reporting information in FIG. 8D and the reporting information in FIG. 8E is applied when a polygon that surrounds the region of interest is a diamond, and the reporting information in FIG. 8D is applied when the sets of coordinates of the vertexes of the diamond are set as the sets of coordinates of interest whereas the reporting information in FIG. 8E is applied when the sets of coordinates of midpoints of the respective sides of the diamond are set as the sets of coordinates of interest.

Figure 9:
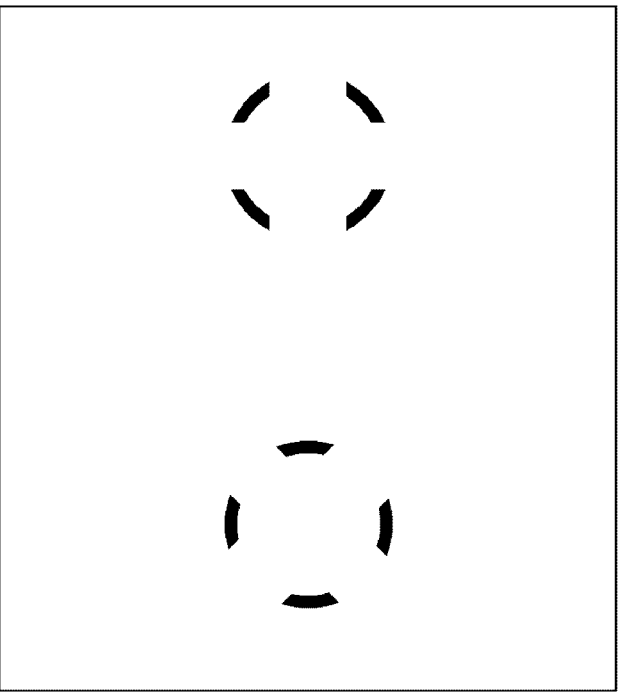
FIG. 9 illustrates two types of reporting information displayed on an outline of a circle that surrounds the region of interest.

FIG. 9 illustrates two types of reporting information (figures) displayed on an outline of a circle that surrounds the region of interest.

Each of the two types of reporting information illustrated in FIG. 9 is applied when sets of coordinates of points at which a circumference of a circle that surrounds the region of interest is equally divided into a plurality of parts (points at which quarters are obtained in the example in FIG. 9) are set as the sets of coordinates of interest and is constituted by four arc figures.

Figure 10:
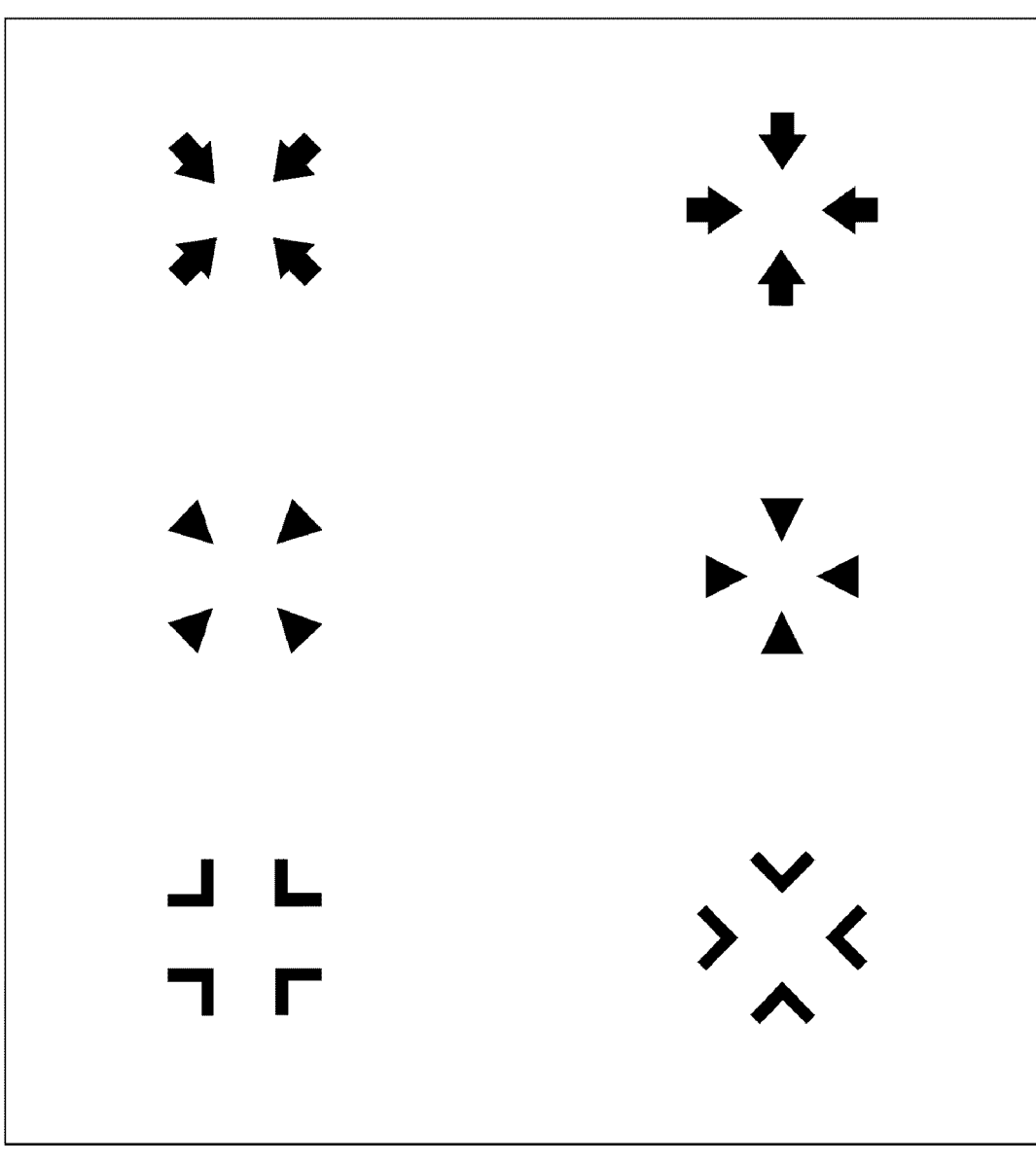
FIG. 10 illustrates six types of reporting information in which positions of tips of a figure are arranged on an outline of a square having a symmetric shape that surrounds the region of interest.

FIG. 10 illustrates six types of reporting information in which positions of tips of a figure are arranged on an outline of a square having a symmetric shape that surrounds the region of interest.

Each type of reporting information illustrated in FIG. 10 is constituted by arrows or figures having the same meaning as arrows.

In the reporting information illustrated in FIG. 10, positions of tips of a plurality of arrows and the like correspond to positions of the sets of coordinates of interest, and the plurality of arrows and the like are arranged to be directed at the region of interest.

Figure 11:
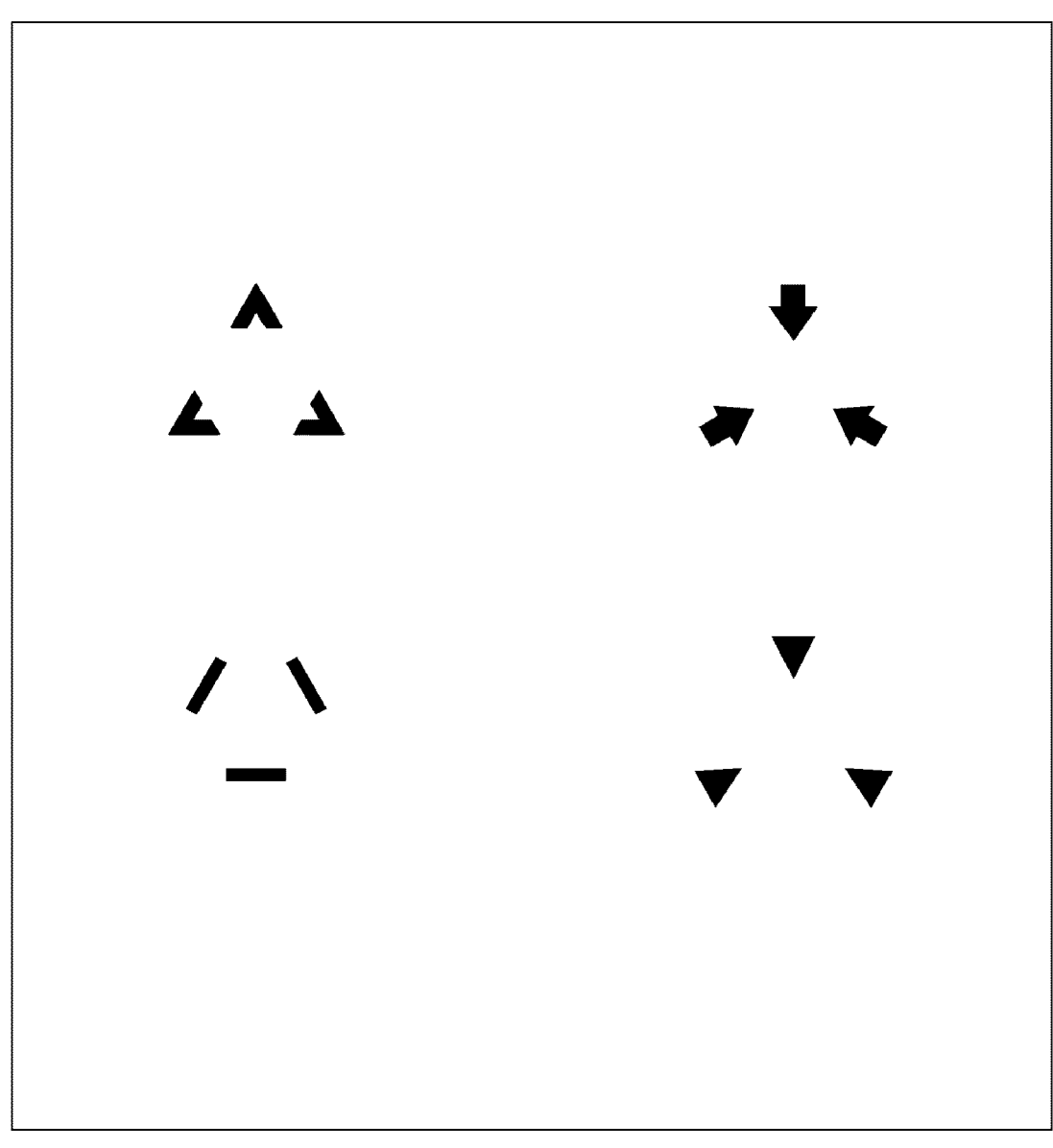
FIG. 11 illustrates four types of reporting information in which each figure is arranged on an outline of a triangle having a symmetric shape that surrounds the region of interest.

FIG. 11 illustrates four types of reporting information in which each figure is arranged on an outline of a triangle having a symmetric shape that surrounds the region of interest.

Each type of reporting information illustrated in FIG. 11 is applied when a polygon that surrounds the region of interest is a triangle (regular triangle) and is constituted by three figures arranged by using vertexes of the regular triangle or midpoints of the respective sides of the regular triangle as the sets of coordinates of interest.

Figure 12A:
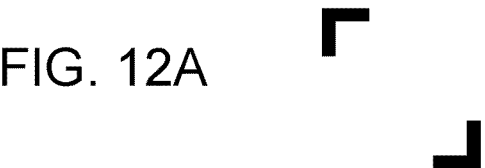
FIG. 12A illustrates reporting information constituted by two figures.
Figure 12B:
FIG. 12B illustrates reporting information constituted by five figures.
Figure 12C:
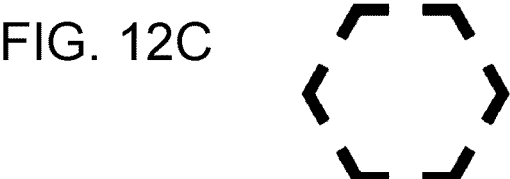
FIG. 12C illustrates reporting information constituted by six figures.

FIG. 12A illustrates reporting information constituted by two figures, FIG. 12B illustrates reporting information constituted by five figures, and FIG. 12C illustrates reporting information constituted by six figures.

The reporting information illustrated in FIG. 12A is reporting information constituted by two figures arranged at diagonal positions of a rectangle that surrounds the region of interest.

The reporting information illustrated in FIG. 12B is applied when a polygon that surrounds the region of interest is a pentagon (regular pentagon), and the reporting information illustrated in FIG. 12C is applied when a polygon that surrounds the region of interest is a hexagon (regular hexagon).

The plurality of figures constituting the reporting information illustrated in FIGS. 8 to 12 are figures obtained by rotating a single figure, as the plurality of figures constituting the reporting information are similar figures.

Figure 13:
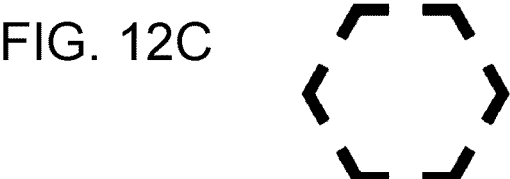
FIG. 13 illustrates reporting information constituted by four figures L1 to L4.

FIG. 13 illustrates reporting information constituted by four figures L1 to L4.

The figures L1 and L3 illustrated in FIG. 13 are point-symmetrical figures. The figure L1 rotated 180 degrees corresponds to the figure L3.

The figures L1 and L2 are line-symmetrical figures, and the figures L1 and L4 are line-symmetrical figures. The figure L1 axially reversed in the horizontal direction in FIG.

13 corresponds to the figure L2, and the figure L1 axially reversed in the vertical direction corresponds to the figure L4.

That is, the four figures L1 to L4 illustrated in FIG. 13 can be generated by rotating or reversing a single figure.

The figure storage unit 50 illustrated in FIG. 2 can store the one or more types of reporting information illustrated in FIGS. 8 to 13. However, by storing only one of the plurality of figures constituting one type of reporting information, and by the reporting information display control unit 45B rotating or reversing the one of the plurality of figures constituting the reporting information, a plurality of figures constituting the reporting information can be acquired and used for a plurality of sets of coordinates of interest. That is, the plurality of figures can be generated from a single figure without individually preparing the figures.

Figure 14:
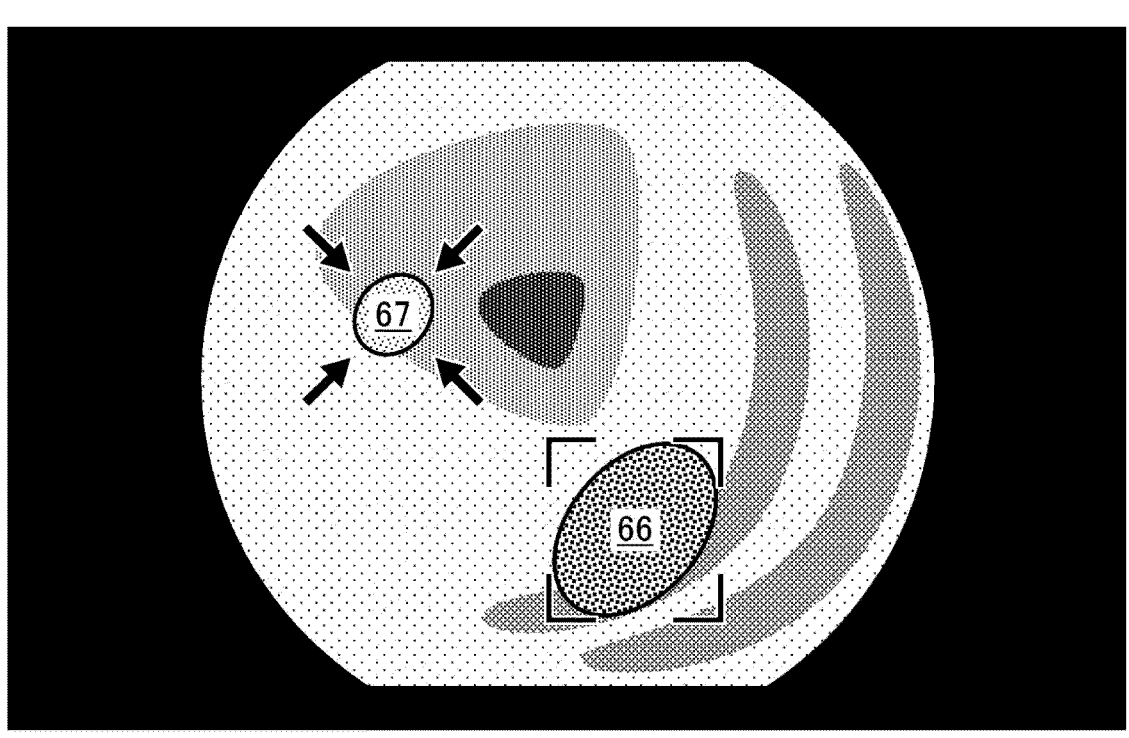
FIG. 14 illustrates another embodiment of an image and reporting information displayed on the display 16.

FIG. 14 illustrates another embodiment of an image and reporting information (figures) displayed on the display 16, and a plurality of regions of interest 66 and 67 are present in the image illustrated in FIG. 14.

If a plurality of regions of interest are present within one frame image, the region-of-interest detecting unit 41 illustrated in FIG. 2 can detect the plurality of regions of interest 66 and 67 concurrently by the CNN.

If the plurality of regions of interest 66 and 67 are detected by the region-of-interest detecting unit 41, the region-of-interest information acquiring unit 42 acquires a plurality of pieces of region-of-interest information indicating the regions of interest 66 and 67 from the region-of-interest detecting unit 41. Upon acquiring the plurality of pieces of region-of-interest information from the region-of-interest information acquiring unit 42, on the basis of the acquired plurality of pieces of region-of-interest information, the coordinates calculating unit 43 calculates a plurality of sets of coordinates of interest surrounding the regions of interest for each of the plurality of regions of interest 66 and 67.

Upon the region-of-interest information acquiring unit 42 acquiring the plurality of pieces of region-of-interest information corresponding to the plurality of regions of interest 66 and 67, the reporting information display control unit 45B adds reporting information to each of the plurality of regions of interest 66 and 67. In this case, it is preferable to assign the reporting information constituted by figures having different shapes to the plurality of regions of interest 66 and 67.

In the example illustrated in FIG. 14, a plurality of substantially L-shaped figures are assigned to the front-side large region of interest 66, and a plurality of arrow figures are assigned to the deep-side small region of interest 67.

Alternatively, the reporting information display control unit 45B may assign figures having different colors to the plurality of regions of interest when adding the figures to the plurality of regions of interest. In this case, the figures may have an identical shape or different shapes.

Thus, it becomes easy to distinguish the plurality of regions of interest by the figures having different shapes or different colors, and it becomes easy to visually follow the plurality of regions of interest when the plurality of regions of interest move.

Second Embodiment of Medical Image Processing Device 14

Figure 15:
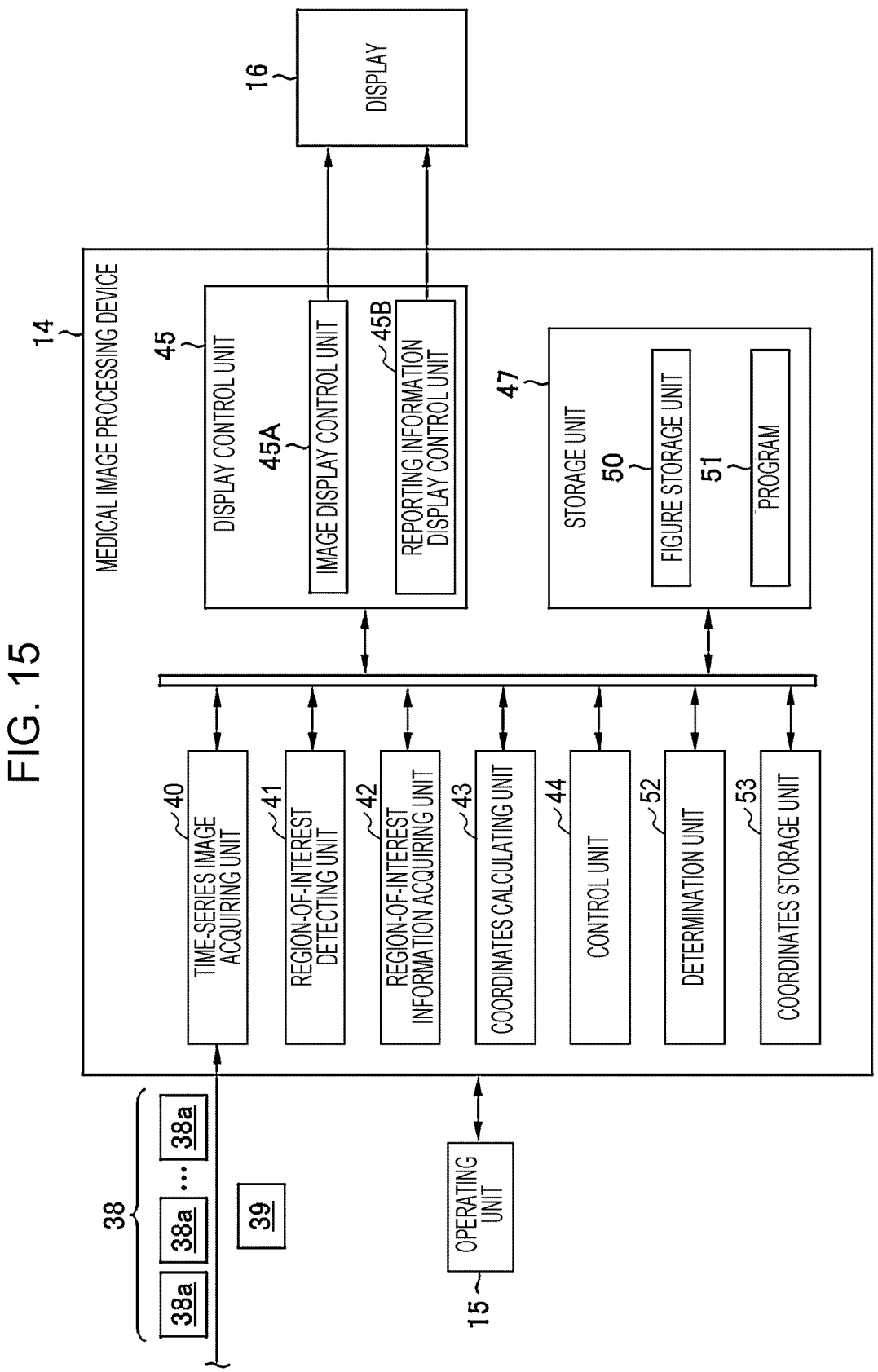
FIG. 15 is a block diagram illustrating a second embodiment of the medical image processing device 14.

FIG. 15 is a block diagram illustrating a second embodiment of the medical image processing device 14. Note that in FIG. 15, parts common to those in the first embodiment of the medical image processing device 14 illustrated in FIG.

2 are denoted by the same reference numerals, and detailed description thereof will be omitted.

In the medical image processing device 14 according to the second embodiment illustrated in FIG. 15, mainly, a function of controlling update of reporting information appropriately in accordance with variations of an image (region of interest) in a time-series image is added, and a determination unit 52 and a coordinates storage unit 53 are added compared with the first embodiment illustrated in FIG. 2.

The coordinates storage unit 53 is a storage unit that stores sets of coordinates of interest (plurality of sets of coordinates of interest) calculated by the coordinates calculating unit 43 as sets of reference coordinates. Note that the sets of reference coordinates are not stored in the coordinates storage unit 53 at the start of displaying reporting information, and the sets of reference coordinates stored in the coordinates storage unit 53 are cleared if no region of interest is present in the image (if no sets of coordinates of interest are calculated by the coordinates calculating unit 43).

The determination unit 52 compares the sets of reference coordinates stored in the coordinates storage unit 53 and the sets of coordinates of interest calculated by the coordinates calculating unit 43 with each other and determines whether a change amount between the sets of reference coordinates and the sets of coordinates of interest exceeds a threshold.

If reporting information constituted by the L-shaped four figures S1 to S4 illustrated in FIG. 3 is displayed, the four sets of coordinates of interest P1 to P4 are calculated, and thus, four change amounts (distances between corresponding coordinates) between the sets of reference coordinates and the sets of coordinates of interest can be obtained. The determination unit 52 determines whether at least one of the plurality of change amounts obtained in this manner exceeds a threshold. In a case where the image has a horizontal direction size of 1280 pixels and a vertical direction size of 1024 pixels, the threshold for the change amount is preferably 8 pixels.

If the determination unit 52 determines that the change amount is less than or equal to the threshold, the reporting information display control unit 45B superposes the figures (reporting information) on the basis of the sets of reference coordinates stored in the coordinates storage unit 53. If the determination unit 52 determines that the change amount exceeds the threshold, the reporting information display control unit 45B superposes the figures on the basis of the sets of coordinates of interest calculated by the coordinates calculating unit 43 (sets of coordinates of interest calculated for the image that is currently being displayed) and updates the sets of reference coordinates stored in the coordinates storage unit 53 to the sets of coordinates of interest calculated by the coordinates calculating unit 43.

Although the size or position of the region of interest in the time-series image may vary over time, by updating display of the reporting information that reports the region of interest in the above manner, if the change amount of the size or position of the region of interest is small, the reporting information is fixed. This prevents the reporting information from frequently moving and becoming difficult to observe.

As a first modification of the second embodiment, the coordinates storage unit 53 stores sets of coordinates of interest calculated by the coordinates calculating unit 43 as sets of reference coordinates and stores coordinates located at the center of the sets of reference coordinates (plurality of sets of reference coordinates) as first center coordinates.

Note that it is needless to say that the first center coordinates correspond to the center of a polygon or circle having a symmetric shape that surrounds a region of interest.

The determination unit 52 compares the first center coordinates stored in the coordinates storage unit 53 and second center coordinates located at the center of the coordinates of interest calculated by the coordinates calculating unit 43 with each other and determines whether a change amount between the first center coordinates and the second center coordinates exceeds the threshold. Note that the second center coordinates correspond to the center of a polygon or circle having a symmetric shape that surrounds the region of interest in an image that is currently being displayed.

If the determination unit 52 determines that the change amount is less than or equal to the threshold, the reporting information display control unit 45B superposes figures (reporting information) on the basis of the sets of reference coordinates stored in the coordinates storage unit 53. If the determination unit 52 determines that the change amount exceeds the threshold, the reporting information display control unit 45B superposes figures on the basis of the sets of coordinates of interest calculated by the coordinates calculating unit 43 (sets of coordinates of interest calculated for the image that is currently being displayed) and updates the sets of reference coordinates and first center coordinates stored in the coordinates storage unit 53 to the sets of coordinates of interest calculated by the coordinates calculating unit 43 and the second center coordinates.

For example, while the region of interest is captured on the optical axis of the objective lens of the distal end part 27 of the endoscope 10, if the distal end part 27 of the endoscope 10 is moved in the optical axis direction of the objective lens, the size of the region of interest within the time-series image changes, but the region of interest does not move.

According to the first modification of the second embodiment, if the endoscope 10 is operated in the above manner, the display position of the reporting information (figures) on the screen is kept without being updated, and thus, the reporting information can be moved relatively away from or relatively close to the region of interest, making it easy to compare the region of interest and its peripheral region with each other.

Furthermore, as a second modification of the second embodiment, as in the second embodiment, the coordinates storage unit 53 stores sets of coordinates of interest (plurality of sets of coordinates of interest) calculated by the coordinates calculating unit 43 as sets of reference coordinates.

The determination unit 52 compares the sets of reference coordinates stored in the coordinates storage unit 53 and the sets of coordinates of interest calculated by the coordinates calculating unit 43 with each other and determines whether the sets of coordinates of interest are within the sets of reference coordinates. Herein, a case where the sets of coordinates of interest are within the sets of reference coordinates refers to, for example, a case where all of the sets of coordinates of interest (plurality of sets of center coordinates) are included inside an outline of a polygon or a circle having a symmetric shape that surrounds the region of interest, specified on the basis of the sets of reference coordinates (plurality of sets of reference coordinates).

If the determination unit 52 determines that all of the sets of coordinates of interest (plurality of sets of center coordinates) are included inside an outline of a polygon or a circle having a symmetric shape that surrounds the region of interest, the reporting information display control unit 45B superposes figures on the basis of the sets of reference coordinates stored in the coordinates storage unit 53. If the determination unit 52 determines that all of the sets of coordinates of interest (plurality of sets of center coordinates) are outside an outline of a polygon or a circle having a symmetric shape that surrounds the region of interest, the reporting information display control unit 45B superposes figures (reporting information) on the basis of the sets of coordinates of interest calculated by the coordinates calculating unit 43 and updates the sets of reference coordinates stored in the coordinates storage unit 53 to the sets of coordinates of interest calculated by the coordinates calculating unit 43.

For example, in a case where the distal end part 27 of the endoscope 10 is made to be close to the region of interest to enlarge and display the region of interest for observation of the region of interest, the figures (reporting information) displayed in the peripheral region of the region of interest may hinder comparison between the region of interest and its peripheral region with each other. In this case, when the distal end part 27 of the endoscope 10 is moved slightly away from the region of interest (when the displayed region of interest is reduced), the display position of the reporting information on the screen is kept without being updated.

According to the second modification of the second embodiment, if the endoscope 10 is operated in the above manner, the reporting information can be moved relatively away from the region of interest, making it easy to compare the region of interest and its peripheral region with each other.

Medical Image Processing Method

Figure 16:
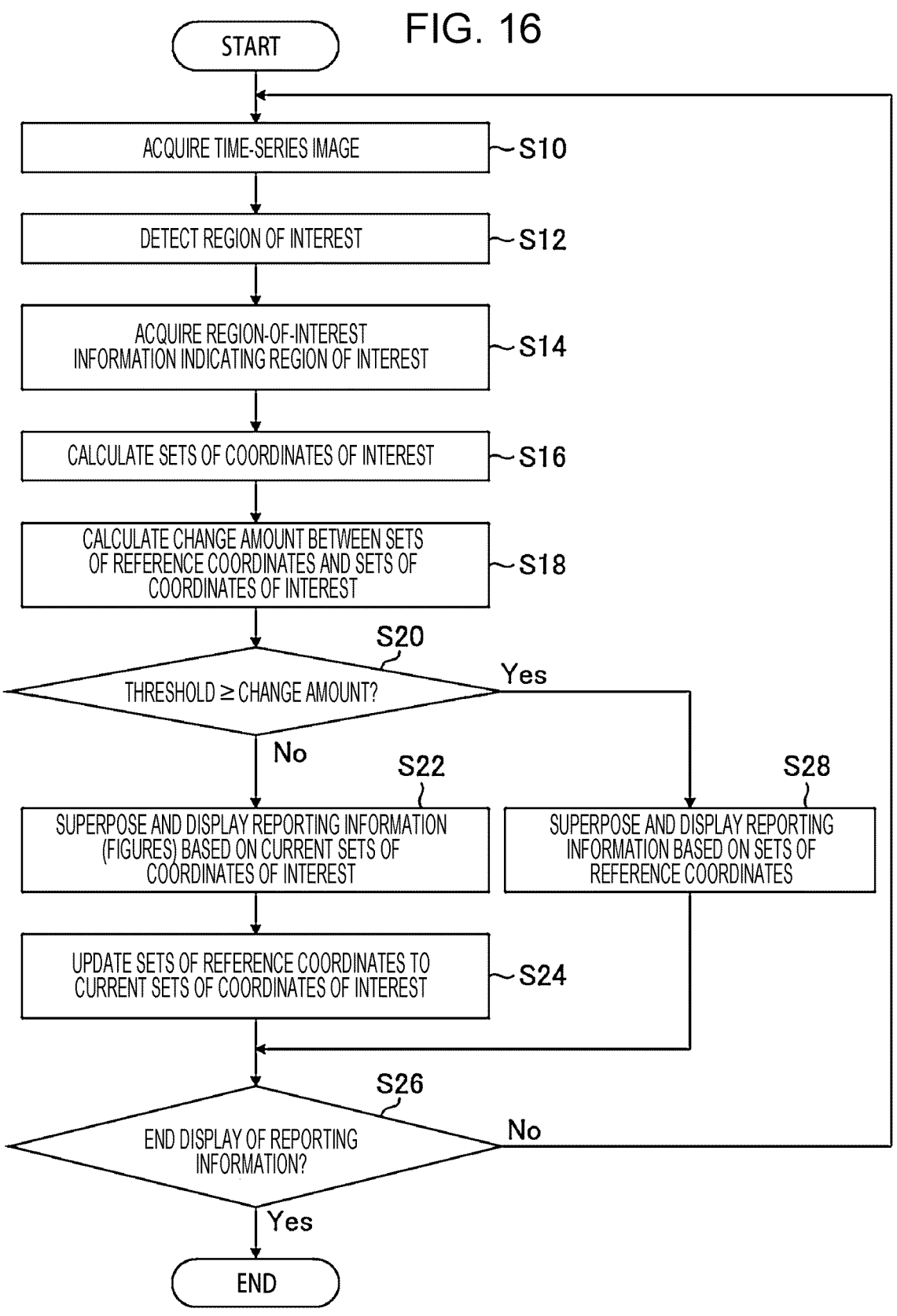
FIG. 16 is a flowchart illustrating an embodiment of a medical image processing method according to the present invention.

FIG. 16 is a flowchart illustrating an embodiment of a medical image processing method according to the present invention and indicates a processing procedure of each unit of the medical image processing device 14 according to the second embodiment illustrated in FIG. 15.

In FIG. 16, the time-series image acquiring unit 40 acquires a time-series image (in this embodiment, the moving image 38 picked up by the endoscope 10) including a photographic subject image from the endoscope processor device 12 (step S10).

The region-of-interest detecting unit 41 sequentially inputs time-series images acquired in step S10, detects a region of interest in the images by the CNN (step S12), and if the region-of-interest detecting unit 41 detects a region of interest, the region-of-interest information acquiring unit 42 acquires region-of-interest information indicating the region of interest from the region-of-interest detecting unit 41 (step S14).

The coordinates calculating unit 43 acquires the region-of-interest information from the region-of-interest information acquiring unit 42 and, on the basis of the acquired region-of-interest information, calculates a plurality of sets of coordinates of interest on an outline of a polygon or circle having a symmetric shape that surrounds the region of interest (step S16).

The determination unit 52 compares sets of reference coordinates stored in the coordinates storage unit 53 and the sets of coordinates of interest calculated by the coordinates calculating unit 43 with each other, calculates a change amount between the sets of reference coordinates and the sets of coordinates of interest (step S18), and determines whether the calculated change amount exceeds a threshold (step S20). Herein, the coordinates storage unit 53 stores sets of coordinates of interest (plurality of sets of coordinates of interest) calculated by the coordinates calculating unit 43 as the sets of reference coordinates. Note that the sets of reference coordinates are not stored in the coordinates storage unit 53 at the start of displaying reporting information, and the sets of reference coordinates stored in the coordinates storage unit 53 are cleared if no region of interest is present in the image (if no sets of coordinates of interest are calculated by the coordinates calculating unit 43).

If the determination unit 52 determines that the change amount exceeds the threshold (in a case of "No"), the reporting information display control unit 45B superposes and displays the reporting information (figures) on the basis of the sets of coordinates of interest calculated by the coordinates calculating unit 43 (sets of coordinates of interest calculated for the image that is currently being displayed) (step S22) and updates the sets of reference coordinates stored in the coordinates storage unit 53 to current sets of coordinates of interest calculated by the coordinates calculating unit 43 (step S24).

On the other hand, if the determination unit 52 determines that the change amount is less than or equal to the threshold (in a case of "Yes"), the reporting information display control unit 45B superposes and displays the figures (reporting information) on the basis of the sets of reference coordinates stored in the coordinates storage unit 53 (step S28).

Subsequently, the control unit 44 determines whether display of the reporting information is to end on the basis of input from the operating unit 15 or the like (step S26). If the display is not to end, the control unit 44 returns to step S10 to repeatedly perform the processing from step S10 to step S26. If the display of the reporting information is to end, the control unit 44 ends this medical image processing.
Miscellaneous In the medical image processing device 14 according to the above embodiments, the time-series image acquiring unit 40 and the region-of-interest detecting unit 41 may not be provided, and the region-of-interest information acquiring unit 42 may externally acquire the region-of-interest information indicating the region of interest in the time-series image. In addition, the image display control unit 45A may not be provided, and the reporting information generated by the reporting information display control unit 45B may be superposed and displayed on the time-series image (moving image) displayed by the endoscope processor device 12.

In addition, although the endoscope processor device 12 and the medical image processing device 14 are provided independently of each other in the above embodiments, the endoscope processor device 12 and the medical image processing device 14 may also be integrated. That is, the functions of the medical image processing device 14 may be provided in the endoscope processor device 12.

Furthermore, a hardware configuration that performs various controls of the medical image processing device 14 in the above embodiments is any of the following various processors. Various processors include a central processing unit (CPU) that is a general-purpose processor functioning as various processing units by executing software (programs), a programmable logic device (PLD) that is a processor in which the circuit configuration is changeable after manufacture, such as field programmable gate array (FPGA), a dedicated electric circuit that is a processor having a circuit configuration that is specially designed to execute specific processing, such as an application specific integrated circuit (ASIC), and the like.

One processing unit may be constituted by one of these various processors, or may be constituted by two or more processors of the same type or different types (e.g., a combination of a plurality of FPGAs or a combination of a CPU and an FPGA). In addition, a plurality of control units may be constituted by one processor. As a first example for constituting a plurality of control units with one processor, one processor may be constituted by a combination of one or more CPUs and software, and this processor may function as a plurality of control units, as typified by a computer such as a client or a server. As a second example, a processor may be used that implements the functions of the entire system including a plurality of control units with one integrated circuit (IC) chip, as typified by a system on chip (SoC) or the like. In this manner, various control units are constituted by one or more of the above various processors in terms of hardware configuration.

In addition, although the time-series image picked up by the endoscope 10 is a medical image to which the present invention is applied in the above embodiments, without limitation thereto, for example, any medical image may be used as long as the medical image is acquired by an ultrasound diagnostic apparatus, a computed tomography (CT) apparatus, a magnetic resonance imaging (MRI) apparatus, or the like and is output continuously.

Furthermore, it is needless to say that the present invention is not limited to the above-described embodiments, and various modifications may be made without departing from the spirit of the present invention.

REFERENCE SIGNS LIST

9 endoscope system
10 endoscope
11 light source device
12 endoscope processor device
13 display device
14 medical image processing device
15 operating unit
16 display
20 insertion part
21 handheld operating unit
22 universal cord
25 soft part
26 bending part
27 distal end part
28 imaging element
29 bending operation knob
30 air/water supply button
31 suction button
32 still image pick-up command unit
33 treatment tool introduction port
35 light guide
36 signal cable
37*a*, 37*b* connector
38 moving image
38*a* frame image
39 still image
40 time-series image acquiring unit
41 region-of-interest detecting unit
42 region-of-interest information acquiring unit
43 coordinates calculating unit
44 control unit
45 display control unit
45A image display control unit
45B reporting information display control unit
47 storage unit
50 figure storage unit
51 program

52 determination unit
53 coordinates storage unit
60, 61, 62, 63, 64, 66, 67 region of interest
L1 to L4, S1 to S4 figure
P1 to P4 set of coordinates of interest
S10 to S28 step

What is claimed is:

1. A medical image processing device comprising:
   one or more processors configured to
   acquire a plurality of images constituting a moving image
      captured in a time series by an endoscope, wherein the
      plurality of images includes a first image and a second
      image captured after the first image;
   output the images to a display device, and displaying the
      moving image on the display device;
   detect a region of interest in the first image and output first
      coordinate information indicating a position of the
      region of interest in the first image;
   superpose and display a first frame on the moving image
      displayed on the display device according to the first
      coordinate information;
   store the first coordinate information as a reference coor-
      dinate information on a memory;
   detect a region of interest in the second image and output
      second coordinate information indicating a position of
      the region of interest in the second image;
   superpose and display, after displaying the first frame, a
      second frame on the moving image displayed on the
      display device according to the reference coordinate
      information or the second coordinate information in
      accordance with a change amount of a size or position
      between the region of interest of the first image and the
      region of interest of the second image calculated from
      the reference coordinate information and the second
      coordinate information; and
   in response to displaying the second frame according to
      the second coordinate information, update the reference
      coordinate information stored in the memory by using
      the second coordinate information.

2. The medical image processing device according to
claim 1, wherein the one or more processors is configured to
   detect a lesion, a treatment scar, or a treatment tool in the
      first image as the region of interest of the first image;
      and
   detect a lesion, a treatment scar, or a treatment tool in the
      second image as the region of interest of the second
      image.

3. The medical image processing device according to
claim 2, wherein the one or more processors is configured to
detect the region of interest of the first image and the region
of interest of the second image by using a trained neural
network.

4. The medical image processing device according to
claim 2, wherein the one or more processors is configured to
classify and detect the region of interest of the first image
and the region of interest of the second image by category.

5. The medical image processing device according to
claim 1, wherein the one or more processors is configured to
display the second frame according to the second coordinate
information in response to determining that the change
amount of the position between the region of interest of the
first image and the region of interest of the second image
exceeds a threshold value.

6. The medical image processing device according to
claim 1, wherein the one or more processors is configured to
display the second frame according to the first coordinate
information in response to determining that the change amount of the size or the position between the region of
interest of the first image and the region of interest of the
second image is less than or equal to a threshold value.

7. The medical image processing device according to
claim 1, wherein the one or more processors is configured to
update the second coordinate information as the reference
coordinate information in response to determining that the
change amount of the size or the position between the region
of interest of the first image and the region of interest of the
second image exceeds a threshold value.

8. The medical image processing device according to
claim 1, wherein the one or more processors is configured to
determine whether the region of interest of the second image
is located inside the region of interest of the first image from
the reference coordinate information and the second coor-
dinate information.

9. The medical image processing device according to
claim 8, wherein the one or more processors is configured to
display the second frame according to the reference coor-
dinate information in response to determining that the region
of interest of the second image is located inside the region
of interest of the first image.

10. The medical image processing device according to
claim 1, wherein
   the first coordinate information includes a plurality of
      coordinate information on an outline of a polygon or
      circle surrounding the region of interest of the first
      image, and
   the second coordinate information includes a plurality of
      coordinate information on an outline of a polygon or
      circle surrounding the region of interest of the second
      image.

11. The medical image processing device according to
claim 1, wherein
   the first coordinate information includes information on a
      center position of the region of interest of the first
      image, and
   the second coordinate information includes information
      on the center position of the region of interest of the
      second image.

12. The medical image processing device according to
claim 1, wherein each of the first frame and the second frame
includes four or more figures.

13. An endoscope system comprising:
   the endoscope according to claim 1;
   an endoscope processor device, configured to control
      operation of the endoscope to generate the plurality of
      images
   the medical image processing device according to claim
      1, configured to acquire the plurality of images from the
      endoscope processor device.

14. A medical image processing method comprising:
   acquiring a plurality of images constituting a moving
      image captured in a time series by an endoscope,
      wherein the plurality of images includes a first image
      and a second image captured after the first image;
   outputting the images to a display device, and displaying
      the moving image on the display device;
   detecting a region of interest in the first image and output
      first coordinate information indicating a position of the
      region of interest in the first image;
   superposing and displaying a first frame on the moving
      image displayed on the display device according to the
      first coordinate information on a display device;
   storing the first coordinate information as a reference
      coordinate information on a memory;

detecting a region of interest in the second image and output second coordinate information indicating a position of the region of interest in the second image;

superposing and displaying, after displaying the first frame, a second frame on the moving image displayed on the display device according to the reference coordinate information or the second coordinate information in accordance with a change amount of a size or position between the region of interest of the first image and the region of interest of the second image calculated from the reference coordinate information and the second coordinate information; and in response to displaying the second frame according to the second coordinate information, updating the second coordinate information as the reference coordinate information stored in the memory.

15. The medical image processing method according to claim 14, wherein each of the region of interest of the first image and the region of interest of the second image includes a lesion, a treatment scar, or a treatment tool.

16. The medical image processing method according to claim 14, wherein displaying the second frame comprises:

in response to determining that the change amount of the position between the region of interest of the first image and the region of interest of the second image exceeds a threshold value, displaying the second frame according to the second coordinate information; and in response to determining that the change amount of the size or the position between the region of interest of the first image and the region of interest of the second image is less than or equal to the threshold value, displaying the second frame according to the first coordinate information, wherein the medical image processing method further comprises:

in response to determining that the change amount of the position between the region of interest of the first image and the region of interest of the second image exceeds the threshold value, updating the second coordinate information as the reference coordinate information.

17. The medical image processing method according to claim 14, further comprising:

determining whether the region of interest of the second image is located inside the region of interest of the first image from the reference coordinate information and the second coordinate information, wherein displaying the second frame comprises:

in response to determining that the region of interest of the second image is located inside the region of interest of the first image, displaying the second frame according to the reference coordinate information.

18. The medical image processing method according to claim 14, wherein the first coordinate information includes a plurality of coordinate information on an outline of a polygon or circle surrounding the region of interest of the first image, and the second coordinate information includes a plurality of coordinate information on an outline of a polygon or circle surrounding the region of interest of the second image.

19. The medical image processing method according to claim 14, wherein the first coordinate information includes information on a center position of the region of interest of the first image, and the second coordinate information includes information on the center position of the region of interest of the second image.

20. The medical image processing method according to claim 14, wherein each of the first frame and the second frame includes four or more figures.

* * * * *